United States Patent
Vlasuk

(10) Patent No.: US 7,329,640 B2
(45) Date of Patent: *Feb. 12, 2008

(54) METHOD OF TREATMENT OF HEMORRHAGIC DISEASE USING A FACTOR VIIA/TISSUE FACTOR INHIBITOR

(75) Inventor: George P. Vlasuk, Carlsbad, CA (US)

(73) Assignee: Dendreon Corporation, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/520,079

(22) Filed: Sep. 12, 2006

(65) Prior Publication Data

US 2007/0010449 A1 Jan. 11, 2007

Related U.S. Application Data

(63) Continuation of application No. 10/431,629, filed on May 6, 2003, now Pat. No. 7,132,398.

(51) Int. Cl.
C07K 14/00 (2006.01)
(52) U.S. Cl. ............................ 514/2; 530/350; 530/300
(58) Field of Classification Search .................... 514/2; 530/350, 380, 300
See application file for complete search history.

(56) References Cited

U.S. PATENT DOCUMENTS

| | | | |
|---|---|---|---|
| 5,650,391 | A | 7/1997 | Schwartz et al. |
| 5,863,894 | A | 1/1999 | Vlasuk et al. |
| 5,864,009 | A | 1/1999 | Vlasuk |
| 5,866,542 | A | 2/1999 | Vlasuk |
| 5,866,543 | A | 2/1999 | Vlasuk |
| 5,872,098 | A | 2/1999 | Vlasuk |
| 5,902,582 | A | 5/1999 | Hung |
| 5,945,275 | A | 8/1999 | Vlasuk |
| 5,955,294 | A | 9/1999 | Vlasuk |
| 6,040,441 | A | 3/2000 | Vlasuk |
| 6,046,318 | A | 4/2000 | Vlasuk |
| 6,063,764 | A | 5/2000 | Creasey et al. |
| 6,087,487 | A | 7/2000 | Vlasuk |
| 6,090,916 | A | 7/2000 | Vlasuk |
| 6,096,877 | A | 8/2000 | Vlasuk |
| 6,121,435 | A | 9/2000 | Vlasuk |
| 6,270,764 | B1 | 8/2001 | Fisher et al. |
| 6,300,100 | B1 | 10/2001 | Kamei et al. |
| 6,303,295 | B1 | 10/2001 | Taylor et al. |
| RE38,008 | E | 2/2003 | Abrams et al. |
| 6,524,567 | B2 | 2/2003 | Laub |
| 6,534,629 | B1 | 3/2003 | Vlasuk |
| 6,872,808 | B1 | 3/2005 | Vlasuk et al. |
| 7,132,398 | B2 | 11/2006 | Vlasuk |
| 2001/0018204 | A1 | 8/2001 | Papathanassiu et al. |
| 2001/0028880 | A1 | 10/2001 | Fisher et al. |
| 2001/0036932 | A1 | 11/2001 | Cardin et al. |
| 2002/0077276 | A1 | 6/2002 | Fredeking et al. |
| 2002/0164582 | A1 | 11/2002 | Hart et al. |

FOREIGN PATENT DOCUMENTS

| | | |
|---|---|---|
| WO | WO 00/30677 | 6/2000 |
| WO | WO 02/069960 A2 | 9/2002 |

OTHER PUBLICATIONS

Abraham, et al., "Assesment of the Safety of Recombinant ZTissue Factor Pathway Inhibitor in Patents with Severe Sepsis: A Multicenter, Randomized, Placebo-Controlled, Single Blind, Dose Escalation Study," *Crit Care Med* 29(11):2081-2089 (2001).
Baize, et al., "Inflammatory Response in Ebola Virus-Infected Patients," *Clin Exp Immunol* 128:163-168 (2002).
Bajaj, et al., "Structure and Biology of Tissue Factor Pathway Inhibitor," *Thromb Haemost* 86:959-972 (2001).
Baugh, et al., "Regulation of Extrinsic Pathway Factor Xa Formation by Tissue Factor Pathway Inhibitor," *J Biol Chem* 273:4378-4386 (1998).
Bernard, et al., "Efficacy and Safety of Recombinant Human Activated Protein C for Severe Sepsis," *N Engl J Med* 344:699-709 (2001).
Bock, et al., "Isolation of Human Blood Coagulation a_Factor Xa by Soybean Trypsin Inhibitor-Sepharose Chromatography and its Actice-Site Titration with Flourescein Mono-P-Guanidinobenzoate," *Archives of Biochem Biophys* 273:375 (1989).
Borio, et al., "Hemorrhagic Fever Viruses as Biological Weapons," JAMA 287(18):2391-2405 (2002).
Bouwman, et al., "Procoagulaent and Inflammatory Response of Virus-Infected Monocytes," *European J Clin Invest* 32:759-766 (2002).
Bray, et al., "Expirometral Therapy of Filovirus Infections," *Antiviral Res* 54:1-17 (2002).
Carson "Computerized Analysis of Enzyme Cascade Reactions Using Continuous Rate Data Obtained with an ELISA Reader," *S.D. Comput Prog Biomed* 19:151-157 (1985).
Creasey, et al., "Tissue Factor Pathway Inhibitor Reduces Mortality From *Escherichia coli* Septic Shock," J Clin Invest 91(6):2850-2860 (1993).
Day, et al., "Recombinant Lippoprotein_Associated Coagulation Inhibitor Inhibits Tissue Thromboplastin-Induced . . . " *Blood* 76(8):1538-1545 (1990).
deJonge, et al., "Tissue Factor Pathway Inhibitor Does not Influence Inflammatory Pathways During Human Endotoxemia," *J Infect Dis* 183(12):1815-1818 (2001).
Despreaux, et al., "the dscA Gene of *Bacillus stearothermophilus* Coding for D-Alanine Carboxypeptidase: Cloning, Structure and Expression in *Escherichai coli* and *Pichia pastoris*," *Gene* 131(1):35-41 (1993).

(Continued)

Primary Examiner—Karen Cochrane Carlson
(74) Attorney, Agent, or Firm—Robins & Pasternak LLP

(57) ABSTRACT

The present invention provides methods of treating hemorrhagic fevers where selective inhibitors of fVIIa/TF are used as a treatment for hemorrhagic fevers and have therapeutic effects which include ameliorating and/or preventing coagulopathy and inflammatory responses. These inhibitors include certain proteins which are part of a family termed Nematode-Extracted Anticoagulant Proteins ("NAPs"). Other inhibitors include Tissue Factor Pathway Inhibitor ("TFPI") and TFPI analogs.

15 Claims, 1 Drawing Sheet

OTHER PUBLICATIONS

Doshi, et al., Evolving Role of Tissue Factor and Its Pathway Inhibitor, *Crit Care Med 30*(5):5241-5250 (2002).

Esmon, "Protein C Pathway in Sepsis," *Annals of Medicine 34*:598-605 (2002).

Esmon, et al., "Role of Coagulation Inhibitors in Inflammation," *Thromb Haemost 86*:51-56 (2001).

Fisher-Hoch, et al., "Pathophysiology of Shock and Hemorrhage in a Fulminating Viral Infection (Ebola)," *J Infect Dis 152*(5):887-894 (1985).

Geisbert, et al., "Evaluation in Nonhuman Primates of Vaccines against Ebola Virus," *Emerging Infectious Diseases 8*:503-507 (2002).

Hensley, et al., "Proinflammatory Response during Ebola Virus Infection of Primates Models: Possible Involvement of the Tumor Necrosis Factor Receptor Superfamily," *Immunology Letters 80*:169-179 (2002).

Jespers, et al., "Surface Expression and Ligand-Based Selection of cDNAs Fused to Filamentous Phage Gene VI," *Biotechnology 13*:378-382 (1995).

Kilgore, et al., "Prospects for the Control of Bolivian Hemorrhagic Fever," *Emerging Infect Dis 1*(3):97-100 (1995).

Klenk, et al., "Symposium on Marburg and Ebola Viruses," Meeting Report, *Virus Res 80*:117-123 (2001).

Laroche, et al., "High-Level Secretion and Very Efficient Isotopic Labeling of Tick Anticoagulant Peptide (TAP) Expressed in the Methyotrophic Yeast, *Pichia pastoris*," *Biotechnology 12*:1119-1124 (1994).

Leroy, et al., "Human Asymphtomatic Ebola Infection and Strong Inflammatory Response," *The Lancet 355*:2210-2215 (2000).

Moons, et al., "Recombinant Nematode Anticoagulant Protein c2, a Novel Inhibitor of Tissue . . . ," *Thromb Haemost 88*:671-631 (2002).

Morrison and Walsh, "The Behavior and Significance of Slowing Binding Enzyme Inhibitors," *Adv. Enzymol 61*:201-300 (1988).

Mwanatambwe, et al., "Ebola Hemorrhagic Fever (EHF): Mechanism of Transmission and Pathogenecity," *J Nippon Med Sch 68*(5):370-375 (2001).

Okajima, "Regulation of Inflammatory Responses by Natural Anticoagulants," Immunol Rev 184:258-274 (2001).

Ruf, et al., "Mutational Analyisis of Receptor and Cofactor Function of Tissue Factor," *Methods in Enzymol 222*:208-224 (1993).

Sanchez, et al., "Reemergence of Ebola Virus in Africa," *Emerging Infect Dis 1*(3):96-97 (1995).

Schou, et al., "Marburg and Ebola Virus Infections in Laboratory Non-Human Primates: A Literature Review," *Comparative Medicine 50*:108-123 (2000).

Stroher, et al., "Infection and Activation of Monocytes by Marburg and Ebola Viruses," *Journal of Virology 75*(22):11025-11033 (2001).

Takeda, et al., "The Pathogenesis of Ebola Hemorrhagic Fever", *Trends in Microb 9*(10):506-511 (2001).

Taylor, et al., "Active Site Inhibited Factor VIIa (DEGR VIIa) Attenuates the Coagulant and Interleukin-6 and -8 but Not Tumor Necrosis Factor, Reponses of the Baboon to LD100 *Escherichia coli*," *Blood 91*:1609-1615 (1998).

Wilson, et al., "Ebola Virus: The Search for Vaccines and Treatments" *Cell and Mol Life Sciences 58*:1826-1841 (2001).

Weitz, et al., "New Anticoagulant Drugs," Chest 119(1):95S-107S (2001).

SEQUENCE LISTING

<160> NUMBER OF SEQ ID NOS: 6

<210> SEQ ID NO 1
<211> LENGTH: 28
<212> TYPE: DNA
<213> ORGANISM: Artificial Sequence
<220> FEATURE:
<223> OTHER INFORMATION: Primer

```
<400> SEQUENCE: 1
gcgtttaaag caacgatgca gtgtggtg                                          28

<210> SEQ ID NO 2
<211> LENGTH: 46
<212> TYPE: DNA
<213> ORGANISM: Artificial Sequence
<220> FEATURE:
<223> OTHER INFORMATION: Primer

<400> SEQUENCE: 2
cgctctagaa gcttcatggg tttcgagttc cgggatatat aaagtc                      46

<210> SEQ ID NO 3
<211> LENGTH: 84
<212> TYPE: PRT
<213> ORGANISM: Ancyclostoma caninum

<400> SEQUENCE: 3
```

Lys Ala Thr Met Gln Cys Gly Glu Asn Glu Lys Tyr Asp Ser Cys Gly
1               5                   10                  15

Ser Lys Glu Cys Asp Lys Cys Lys Tyr Asp Gly Val Glu Glu
            20                  25                  30

Asp Asp Glu Glu Pro Asn Val Pro Cys Leu Val Arg Val Cys His Gln
        35                  40                  45

Asp Cys Val Cys Glu Glu Gly Phe Tyr Arg Asn Lys Asp Asp Lys Cys
    50                  55                  60

Val Ser Ala Glu Asp Cys Glu Leu Asp Asn Met Asp Phe Ile Tyr Pro
65                  70                  75                  80

Gly Thr Arg Asn

```
<210> SEQ ID NO 4
<211> LENGTH: 85
<212> TYPE: PRT
<213> ORGANISM: Ancyclostoma caninum

<400> SEQUENCE: 4
```

Lys Ala Thr Met Gln Cys Gly Glu Asn Glu Lys Tyr Asp Ser Cys Gly
1               5                   10                  15

Ser Lys Glu Cys Asp Lys Cys Lys Tyr Asp Gly Val Glu Glu
            20                  25                  30

Asp Asp Glu Glu Pro Asn Val Pro Cys Leu Val Arg Val Cys His Gln
        35                  40                  45

Asp Cys Val Cys Glu Glu Gly Phe Tyr Arg Asn Lys Asp Asp Lys Cys
    50                  55                  60

Val Ser Ala Glu Asp Cys Glu Leu Asp Asn Met Asp Phe Ile Tyr Pro
65                  70                  75                  80

Gly Thr Arg Asn Pro
                85

```
<210> SEQ ID NO 5
<211> LENGTH: 5
<212> TYPE: PRT
<213> ORGANISM: Ancyclostoma caninum

<400> SEQUENCE: 5
```

Gly Phe Tyr Arg Asn
1               5

```
<210> SEQ ID NO 6
<211> LENGTH: 7
<212> TYPE: PRT
<213> ORGANISM: Artificial Sequence
<220> FEATURE:
<223> OTHER INFORMATION: Variable sequence
<220> FEATURE:
<221> NAME/KEY: VARIANT
<222> LOCATION: 1, 2
<223> OTHER INFORMATION: Xaa = any amino acid, provided that at least
      one Xaa at location 1 or 2 is Glu or Asp

<400> SEQUENCE: 6

Xaa Xaa Gly Phe Tyr Arg Asn
 1               5
```

METHOD OF TREATMENT OF HEMORRHAGIC DISEASE USING A FACTOR VIIA/TISSUE FACTOR INHIBITOR

CROSS-REFERENCE TO RELATED APPLICATIONS

This application is a continuation application of U.S. patent application Ser. No. 10/431,629, filed May 6, 2003 from which priority is claimed pursuant to 35 U.S.C. §120, which application is hereby incorporated by reference in its entirety.

BACKGROUND AND INTRODUCTION TO THE INVENTION

A number of viruses have been reported to cause lethal hemorrhagic disease in humans and certain other primates. These viruses include viruses from a number of viral families, which include Filoviridae, Arenaviridae, Bunyaviridae, and Flaviridae. In particular the Filoviridae, which include the Ebola and Marburg viruses, have resulted in significant morbidity and mortality in infected populations. At present there are no satisfactory disease specific therapies or vaccines for diseases caused by the Filoviridae.

Patients affected with hemorrhagic fevers develop a severe consumptive disseminated intravascular coagulation.

Disseminated intravascular coagulation (DIC) is typically characterized by wide-spread systematic activation of the coagulation cascade resulting in excess thrombin generation. In addition, activation of the fibrinolytic system coupled with the consumption of coagulation factors results in a depletion of clotting factors and degradation of platelet membrane glycoproteins.

Conventional treatment of DIC has been aimed primarily at treatment of the underlying etiologic disease process and secondarily at the coagulopathy that results in the thrombotic and hemorrhagic manifestations. Reported therapies include replacement therapy of coagulation factors by transfusion of fresh frozen plasma. Heparin has been reported as sometimes used in combination with replacement therapy.

Tissue factor ("TF") is a 47 kDa transmembrane glycoprotein that is the major cellular trigger of blood coagulation under physiologic conditions. The factor VIIa-tissue factor ("fVII/TF") catalytic complex is able to generate factor Xa via direct activation of factor X, and indirectly through the activation of factor IX, thus initiating thrombin generation. It has been reported that tissue factor also plays an important role in disease processes resulting from the activation of the coagulation pathway. For example, TF levels are reported to be elevated during bacterial sepsis and this is believed to contribute directly to the pathogenesis of multiple organ failure (Doshi et al., "Evolving role of tissue factor and its pathway inhibitor", Crit. Care. Med. (2002) 30(5 Suppl): 5241-5250). In addition, a number of viruses have been reported to activate the coagulation system following infection; such activation may also be triggered by the up regulation of TF expression (Bowman, et al., "Procoagulant and inflammatory response of virus-infected monocytes", European J. Clin. Invest. (2002) 32: 759-766; Baugh et al., "Regulation of extrinsic pathway factor Xa formation by tissue factor pathway inhibitor", J. Biol. Chem. (1998) 273: 4378-4386; Taylor et al., "Active site inhibited factor VIIa (DEGR VIIa) attenuates the coagulant and interleukin-6 and -8, but not tumor necrosis factor, responses of the baboon to LD100 *Escherichra coli*", Blood (1998) 91: 1609-1615). A variety of inflammatory stimuli, including bacterial cell products, viral infection and cytokines, have been reported to induce the expression of TF on the surface of endothelial cells and monocytes, thereby activating the coagulation pathway (Doshi, et al.).

Tissue Factor Pathway Inhibitor (TFPI) is an endogenous systemically circulating plasma protein which is said to function as a physiological anticoagulant by inhibiting VIIa/TF complexes and preventing the initiation of coagulation. TFPI contains multiple Kunitz-type protease inhibitor domains, and is the principal physiologic inhibitor of TF/FVIIa. TFPI has been reported to bind to and inhibit factor Xa directly, prior to forming a quaternary inhibitory complex with TF/FVIIa, thereby inhibiting thrombin generation (Baugh et al.). Processes for preparing recombinant TFPI have been reported. See, e.g. U.S. Pat. No. 6,300,100 to Kamel et al.

In addition to its role in initiating coagulation, the TF/FVIIa has been reported to have direct pro-inflammatory effects independent of the activation of coagulation in man (Taylor et al.). In experimental settings where animals were depleted of TFPI, the animals were reported to have a demonstrated sensitivity to bacterial endotoxin and a higher propensity to develop intravascular coagulation (Doshi et al.). In a lethal *E. coli* sepsis model in baboons, treatment with TFPI was reported to attenuate the procoagulant and inflammatory cytokine interleukin-6 (IL-6) response and to prevent mortality (Creasey et al., "Tissue factor pathway inhibitor reduces mortality from *Escherichia coli* septic shock", J. Clin. Invest. (1993) 91(6): 2850-2860). However, in healthy human volunteers administered low dose bacterial endotoxin, blocking TF/FVIIa with TFPI was reported to have no impact on inflammatory cytokines, but to completely prevent endotoxin-induced activation of coagulation (deJonge et al., "Tissue factor pathway inhibitor does not influence inflammatory pathways during human endotoxemia", J. Infect. Dis. (2001) 183(12): 1815-1818). A phase II clinical trial of recombinant TFPI (rTFPI) in patients with severe sepsis, the rTFPI group was reported to demonstrate accelerated decrease of IL-6 plasma levels (Reinhart et al., "Assessment of the safety of recombinant tissue factor pathway inhibitor in patients with severe sepsis, a multicenter randomized, placebo controlled single blind, dose escalation study", Crit. Clin. Med. (2001) 29(11): 2081-2089). A phase III trial of trifacogin, a rTFPI, in severe sepsis failed to show a reduction in the primary end-point of 28-day all cause mortality (Doshi et al.).

Protein C (PC) is another component of the natural anticoagulant system in mammals. Unlike TFPI, which acts at the level of TF/fVIIa, the PC pathway is reported to inhibit coagulation by down regulating thrombin formation via the proteolytic inactivation of the non-enzymatic co-factors factor Va and factor VIIIa (Esmon C., "Protein C pathway in sepsis", Annals of Medicine (2002) 34:598-605). The active component of the PC pathway is termed activated PC (aPC). aPC is formed by the action of thrombin bound to the non-enzymatic co-factor thrombomodulin. A recombinant form of aPC (drotrecogin alfa) has been reported to reduce the incidence death in patients suffering from severe bacterial sepsis (Bernard et al., "Efficacy and safety of recombinant human activated Protein C for severe sepsis", N. Engl. J. Med. (2001) 344:699-709).

Published United States Patent Application, publication number US 2001/0028880 A1, is said to relate to the treatment of viral hemorrhagic fever with Protein C.

SUMMARY OF THE INVENTION

According to one aspect, the present invention is directed to treatment of viral hemorrhagic fever by administration of a selective inhibitor of the TF/VIIa complex which initiates the activation of coagulation.

In view of the published reports on the effects of inhibiting the TF/VIIa complex by different inhibitors, it is not predictable as to what effects a particular inhibitor of TF/VIIa will have on the associated inflammation responses induced by either bacterial or viral infection. Furthermore, little is known regarding the role of TF in mediating the coagulation and inflammatory responses to viral infection particularly hemorrhagic viral infection.

According to one aspect, the present invention is directed to a method for treating a mammal having a hemorrhagic fever which comprises administering to said mammal an amount of a selective inhibitor of Factor VIIa/tissue factor ("fVIIa/TF") effective to ameliorate symptoms of said fever.

According to an alternate aspect, the present invention is directed to a method of treating a mammal having a hemorrhagic fever which comprises administering to said mammal a therapeutically effective amount of a compound which specifically inhibits the catalytic activity of the fVIIa/TF complex in the presence of Factor Xa ("fXa") or catalytically active fXa derivative (including the zymogen Factor X ("fX")) and does not specifically inhibit the catalytic activity of the fVIIa/TF complex in the absence of fXa or catalytically inactive fXa derivative and does not specifically inhibit the activity of Factor VIIa ("fVIIa") in the absence of tissue factor ("TF") and does not specifically inhibit prothombinase.

In an additional aspect, the present invention is directed to a method of treating coagulopathy and/or an inflammatory response due to hemorrhagic fever in a mammal which comprises administering to said mammal an amount of a selective fVIIa/TF inhibitor effective to decrease or prevent said coagulopathy and/or inflammatory response in said mammal.

The hemorrhagic fever to be treated may be caused by a virus. Such hemorrhagic fevers may be caused by viruses such as the Filoviridae, Arenaviridae Bunyaviridae and Flaviridae. The methods of the present invention may be particularly suited to treat viral hemorrhagic fevers caused by the Filoviridae.

Suitable fVIIa/TF inhibitors and compounds which inhibit the catalytic activity of the fVIIa/TF complex include members of the family of Nematode-Extracted Anti-coagulant Proteins (NAPs") having fVIIa/TF inhibitory activity, tissue factor pathway inhibitor ("TFPI") and analogs of tissue factor pathway inhibitor.

Suitable NAPs for use in the methods of the present invention include an isolated protein having Factor VIIa/TF inhibitory activity and having one or more NAP domains, wherein each NAP domain includes the sequence: Cys-A1-Cys-A2-Cys-A3-Cys-A4-Cys-A5-Cys-A6-Cys-A7-Cys-A8-Cys-A9-Cys-A10, wherein (a) A1 is an amino acid sequence of 7 to 8 amino acid residues;
(b) A2 is an amino acid sequence;
(c) A3 is an amino acid sequence of 3 amino acid residues;
(d) A4 is an amino acid sequence;
(e) A5 is an amino acid sequence of 3 to 4 amino acid residues;
(f) A6 is an amino acid sequence;
(g) A7 is an amino acid residue;
(h) A8 is an amino acid sequence of 11 to 12 amino acid residues;
(i) A9 is an amino acid sequence of 5 to 7 amino acid residues; and A10 is an amino acid sequence; wherein each of A2, A4, A6 and A10 has an independently selected number of independently selected amino acid residues and each sequence is selected such that each NAP domain has in total less than about 120 amino acid residues.

Certain suitable NAPs for use according to the methods of the present invention include AcaNAPc2 (SEQ. ID. NO. 3) and AcaNAPc2/proline (SEQ. ID. NO. 4). Also suitable for use according to the methods of the present invention are TFPI and TFPI analogs.

Definitions

The terms "Factor Xa" or "fXa" or "FXa" are synonymous and are commonly known to mean a serine protease within the blood coagulation cascade of enzymes that functions to form the enzyme thrombin as part of the prothrombinase complex.

The term "catalytically inactive fXa derivative" includes the zymogen Factor X ("fX" or "FX"), as well as other catalytically inactive fXa derivatives.

The phrase "Factor Xa inhibitory activity" means an activity that inhibits the catalytic activity of fXa toward its substrate.

The phrase "Factor Xa selective inhibitory activity" means inhibitory activity that is selective toward Factor Xa compared to other related enzymes, such as other serine proteases.

The phrase "Factor Xa inhibitor" is a compound having Factor Xa inhibitory activity.

The terms "Factor VIIa/Tissue Factor" or "Tissue Factor/Factor VIIa" or "fVIIa/TF" or "FVIIa/TF" or "TF/fVIIa" are synonymous and are commonly known to mean a catalytically active complex of the serine protease coagulation factor VIIa (fVIIa) and the non-enzymatic protein Tissue Factor (TF), wherein the complex is assembled on the surface of a phospholipid membrane of defined composition.

The phrase "fVIIa/TF inhibitory activity" or "TF/fVIIa inhibitory activity" means an activity that inhibits the catalytic activity of the fVIIa/TF complex in the presence of fXa or catalytically inactive fXa derivative (including the zymogen fX). The phrase "fVIIa/TF selective inhibitory activity" means inhibitory activity that is selective toward fVIIa/TF compared to other related enzymes, such as other serine proteases, including FVIIa and fXa.

The phrase a "fVIIa/TF inhibitor" is a compound having fVIIa/TF inhibitory activity in the presence of fXa or catalytically inactive fXa derivatives.

The phrase "serine protease" is commonly known to mean an enzyme with a common three-dimensional fold, comprising a triad of the amino acids histidine, aspartic acid and serine, that catalytically cleaves an amide bond, wherein the serine residue within the triad is involved in a covalent manner in the catalytic cleavage. Serine proteases are rendered catalytically inactive by covalent modification of the serine residue within the catalytic triad by diisopropylflourophosphate (DFP).

The phrase "serine protease inhibitory activity" means an activity that inhibits the catalytic activity of a serine protease.

The phrase "serine protease selective inhibitory activity" means inhibitory activity that is selective toward one serine protease compared to other serine proteases.

The phrase "serine protease inhibitor" is a compound having serine protease inhibitory activity.

The term "prothrombinase" is commonly known to mean a catalytically active complex of the serine protease coagulation Factor Xa (fXa) and the non-enzymatic protein Factor Va (fVa), wherein the complex is assembled on the surface of a phospholipid membrane of defined composition.

The phrase "anticoagulant activity" means an activity that inhibits the clotting of blood, which includes the clotting of plasma.

The terms "selective," "selectivity," and permutations thereof, when referring to activity of a compound or composition toward a certain enzyme, mean that the compound or composition inhibits the specified enzyme with at least 10-fold higher potency that it inhibits other, related enzymes. Thus, the activity of the compound or composition is selective toward that specified enzyme.

The term "substantially the same" when used to refer to proteins, amino acid sequences, cDNAs, nucleotide sequences, and the like refer to proteins, cDNAs or sequences having at least about 80% homology with the other protein, cDNA, or sequence.

The terms "AcaNAPc2" and "rNAPc2" refer to a recombinant protein of the NAP family. The preparation and sequence of AcaNAPc2 is described in U.S. Pat. No. 5,866, 542.

The terms "AcaNAPc2/proline," "AcaNAPc2P," "rNAPc2/proline" and "rNAPc2/Pro" refer to a recombinant protein having the amino acid sequence of AcaNAPc2 which has been modified to add a proline residue to the C-terminus of the sequence of AcaNAPc2.

DETAILED DESCRIPTION OF THE INVENTION

A. Inhibitors of fVIIa/TF

Figure 1:
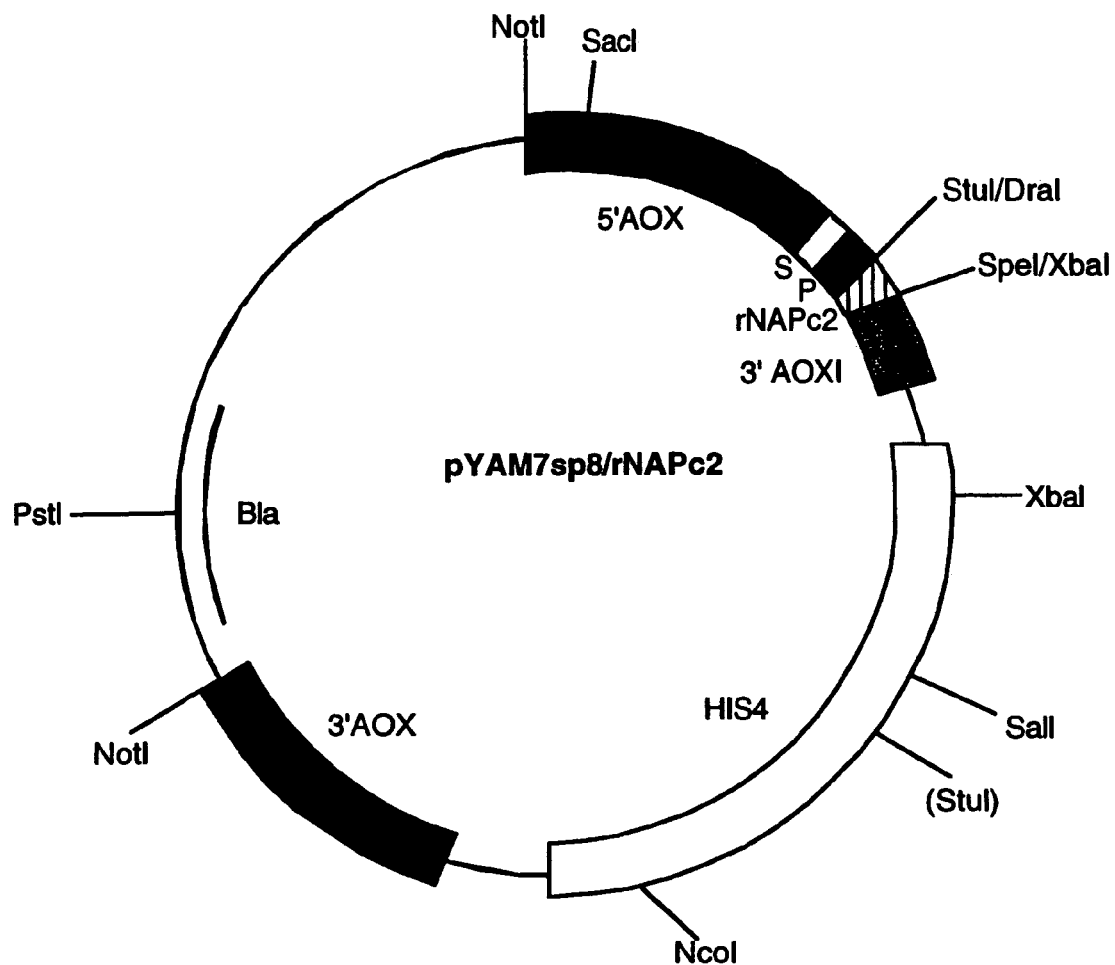
FIG. 1 depicts the expression vector pYAM7sp8/rNAPc2 used in the expression of recombinant AcaNAPc2/proline.

A number of selective inhibitors of fVIIa/TF have been reported. According to one aspect of the present invention, these inhibitors are used as a treatment for hemorrhagic fevers and have therapeutic effects which include ameliorating and/or preventing coagulopathy and inflammatory responses. These inhibitors include certain proteins which are part of a family termed Nematode-Extracted Anticoagulant Proteins ("NAPs"). Other inhibitors include Tissue Factor Pathway Inhibitor ("TFPI") and TFPI analogs.

1. NAP Proteins

U.S. Pat. No. 5,866,542 to Vlasuk et al. describes a family of proteins termed "Nematode-Extracted Anticoagulant Proteins ("NAPs"), one class of which is described as having Factor VIIa/TF inhibitory activity. This class of proteins include an isolated protein having Factor VIIa/TF inhibitory activity and having one or more NAP domains, wherein each NAP domain includes the sequence: Cys-A1-Cys-A2-Cys-A3-Cys-A4-Cys-A5-Cys-A6-Cys-A7-Cys-A8-Cys-A9-Cys-A10 ("FORMULA III"), wherein (a) A1 is an amino acid sequence of 7 to 8 amino acid residues;

(b) A2 is an amino acid sequence;

(c) A3 is an amino acid sequence of 3 amino acid residues;

(d) A4 is an amino acid sequence;

(e) A5 is an amino acid sequence of 3 to 4 amino acid residues;

(f) A6 is an amino acid sequence;

(g) A7 is an amino acid residue;

(h) A8 is an amino acid sequence of 11 to 12 amino acid residues;

(i) A9 is an amino acid sequence of 5 to 7 amino acid residues; and (j) A10 is an amino acid sequence; wherein each of A2, A4, A6 and A10 has an independently selected number of independently selected amino acid residues and each sequence is selected such that each NAP domain has in total less than about 120 amino acid residues.

Suitable NAP proteins within this aspect of the invention have at least one NAP domain. Preferred are NAPs having one or two NAP domains. Preferred are proteins having at least one NAP domain substantially the same as the NAP domain of AcaNAPc2 (SEQ. ID. No. 3). The NAP protein AcaNAPc2 (SEQ. ID. NO. 3) has one NAP domain and is a preferred NAP according to this aspect of the invention. Also preferred is AcaNAPc2/proline (SEQ. ID. NO. 4). AcaNAPc2/proline is a recombinant protein having the sequence of AcaNAPc2 and which has an additional proline residue at the C terminus.

Preferred NAP proteins include those in which A2 is an amino acid sequence of 3 to 5 amino acid residues, A4 is an amino acid sequence of 6 to 19 amino acid residues, A6 is an amino acid sequence of 3 to 5 amino acid residues, and A10 is an amino acid sequence of 5 to 25 amino acid residues.

In certain preferred NAPs, A3 has the sequence Asp-$A3_a$-$A3_b$, wherein $A3_a$ and $A^3_b$ are independently selected amino acid residues. More preferably, A3 is Asp-Lys-Lys.

In certain preferred NAPs, A4 is an amino acid sequence having a net anionic charge.

Also preferred are NAPS where A5 has the sequence $A5_a$-$A5_b$-$A5_c$-$A5_d$ wherein $A5_a$ through $A5_d$ are independently selected amino acid residues. Preferably, $A5_a$ is Leu and $A5_c$ is Arg.

In certain preferred NAPs, a preferred A7 amino acid residue is Val or Ile, more preferably Val.

Certain preferred NAPs include those in which A8 includes the amino acid sequence $A8_a$-$A8_b$-$A8_c$-$A8_d$-$A8_e$-$A8_f$-$A8_g$ wherein (a) $A8_a$ is the first amino acid residue in A8, (b) at least one of $A8_a$ and $A8_b$ is selected from the group consisting of Glu or Asp, and (c) $A8_c$ through $A^8_g$ are independently selected amino acid residues.

Preferably, $A8_c$ is Gly, $A8_d$ is selected from the group consisting of Phe, Tyr, and Leu, $A8_e$ is Tyr, $A8_f$ is Arg, and $A^8_g$ is selected from Asp and Asn. A preferred $A8_c$-$A8_d$-$A8_e$-$A8_f$-$A8_g$ sequence is Gly-Phe-Tyr-Arg-Asn (SEQ. ID. NO. 5).

In one embodiment, the present invention is directed to methods of using a suitable NAP molecule having factor VIIa/tissue factor inhibitory activity wherein (a) A3 has the sequences Asp-$A3_a$-$A3_b$, wherein $A3_a$ and $A3_b$ are independently selected amino acid residues;

(b) A4 is an amino acid sequence having a net anionic charge;

(c) A5 has the sequence $A5_a$-$A5_b$-$A5_c$-$A5_d$, wherein $A5_a$ through $A5_d$ are independently selected amino acid residues, and (d) A7 is selected from the group consisting of Val and Ile.

Use of pharmaceutical compositions comprising one or more of these NAP proteins having factor VIIa/tissue factor inhibitory activity and a pharmaceutically acceptable carrier are contemplated by this embodiment. NAP proteins used according to the methods of the present invention have at least one NAP domain. Preferred are NAPs having one or two NAP domains. The NAP proteins AcaNAPc2 and AcaNAPc2/proline have one NAP domain and are preferred NAPs according to this embodiment of the invention.

In another preferred embodiment, a suitable NAP molecule for use in the methods of the present invention is one wherein (a) A3 is Asp-Lys-Lys;

(b) A4 is an amino acid sequence having a net anionic charge;

(c) A5 has the sequence $A5_a$-$A5_b$-$A5_c$-$A5_d$ wherein $A5_a$ through $A5_d$ are independently selected amino acid residues;

(d) A7 is Val;

(e) A8 includes an amino acid sequence $A8_a$-$A8_b$-Gly-Phe-Tyr-Arg-Asn (SEQ. ID. NO. 6), wherein at least one of $A8_a$ and $A8_b$ is Glu or Asp. Use of pharmaceutical compositions comprising such NAP proteins and a pharmaceutically acceptable carrier also are contemplated by this invention. These NAP proteins have at least one NAP domain. Preferred are NAPs having one or two NAP domains. The NAP proteins AcaNAPc2 (SEQ. ID. NO. 3) and AcaNAPc2/proline (SEQ. ID. NO. 4) each have one NAP domain and are preferred NAPs according to this embodiment of the invention.

Certain preferred NAP proteins having Factor VIIa/TF inhibitory activity as described above are derived from a nematode species. A preferred nematode species is selected from the group consisting of *Ancylostoma caninum, Ancylostoma ceylanicum, Ancylostoma duodenale, Necator americanus*, and *Heligomosomoides polygyrus*. These NAPs may conveniently be prepared by recombinant means. Particularly preferred are the NAP proteins AcaNAPc2 and AcaNAPc2/proline. AcaNAPc2 was derived from *Ancylostoma caninum* using recombinant methods.

U.S. Pat. No. 5,866,542 describes the preparation of recombinant NAP proteins, including AcaNAPc2 and AcaNAPc2/proline.

2. Tissue Factor Pathway Inhibitor

U.S. Pat. No. 6,300,100 describes Tissue Factor Pathway Inhibitor and process for its preparation by recombinant methods.

U.S. Pat. No. 5,378,614 describes the preparation of certain analogs of TFPI.

B. Selection of Compounds Having Factor VIIa/Tissue Factor Inhibitory Activity

The fVIIa/TF inhibitory activity of NAPs and other compounds used according to the methods of the present invention can be determined using protocols described herein. Example 3 describes fVIIa/TF assays. There, the fVIIa/TF-mediated cleavage and liberation of the tritiated activation peptide from radiolabeled human factor IX ($^3$H-FIX) or the amidolytic hydrolysis of a chromogenic peptidyl substrate are measured. Interestingly, certain fVIIa/TF inhibitors require the presence of fXa or catalytically inactive fXa derivative in order to be active fVIIa/TF inhibitors. However, certain NAP and other fVIIa/TF inhibitors were equally effective in the presence of fXa in which the active site had been irreversibly occupied with the peptidyl chloromethyl ketone H-Glu-Gly-Arg-CMK (EGR), and thereby rendered catalytically inactive (EGR-fXa). While not wishing to be bound by any one explanation, it appears that these proteins having fVIIa/TF inhibitory activity form a binary complex with fXa by binding to a specific recognition site on the enzyme that is distinct from the primary recognition sites, $P_4$-$P_1$, within the catalytic center of the enzyme. This is followed by the formation of a quaternary inhibitory complex with the fVIIa/TF complex. Consistent with this hypothesis is that EGR-fXa can fully support the inhibition of fVIIa/TF by these compounds which are inhibitory for fVIIa/TF despite covalent occupancy of the primary recognition sites ($P_4$-$P_1$) within the catalytic site of fXa by the tripeptidyl-chloromethyl ketone (EGR-CMK).

The fVIIa/TF inhibitory activity of these compounds also can be determined using the protocol in Example 7, as well as the fXa assays described above, and in Examples 5 and 6. There, the ability of a compound to inhibit the catalytic activity of a variety of enzymes is measured and compared to its inhibitory activity toward the fVIIa/TF complex.

Certain of these compounds specifically inhibit the catalytic activity of the fVIIa/TF complex in the presence of fXa or catalytically inactive fXa derivative (including the zymogen Factor X), but do not specifically inhibit prothrombinase. Preferred compounds according to this aspect of the invention have the characteristics described above for an isolated protein having Factor VIIa/TF inhibitory activity and having one or more NAP domains. A preferred protein according to this aspect of the invention is AcaNAPc2 or AcaNAPc2/Pro.

These compounds are identified by their fVIIa/TF inhibitory activity in the presence of fXa or a fXa derivative, whether the derivative is catalytically active or not. The protocol in Example 4 can detect a compound's inactivity toward free fXa or prothrombinase. Data generated using the protocols in Example 3 will identify compounds that require either catalytically active or inactive fXa to inhibit fVIIa/TF complex.

C. Administration and Formulation

According to one aspect of the present invention, the fVIIa/TF inhibitor is administered to a patient in need of treatment as soon as the hemorrhagic fever is detected. It may be preferred to treat the patient at as early a stage in the hemorrhagic fever as possible, preferably at or before onset of symptoms. Thus, with respect to hemorrhagic fever-causing viruses it may be advantageous to administer the fVIIa/TF prior to exposure to the virus or as soon after exposure as possible.

The compounds or pharmaceutical compositions thereof used according to the methods of the present invention are administered in vivo, ordinarily in a mammal, preferably in a human. In employing them in vivo, the compounds and pharmaceutical compositions can be administered to a mammal in a variety of ways, including orally, parenterally, intravenously, subcutaneously, intramuscularly, colonically, rectally, nasally or intraperitoneally, employing a variety of dosage forms. Administration is preferably parenteral, such as intravenous on a daily basis. Alternatively, for some compounds or pharmaceutical compositions administration is preferably oral, such as by tablets, capsules or elixirs taken on a daily basis.

In practicing the methods of the present invention, the compounds or pharmaceutical compositions used according to the methods of the present invention are administered alone or in combination with one another, or in combination with other therapeutic or in vivo diagnostic agents.

As is apparent to one skilled in the medical art, a therapeutically effective amount of the compounds or pharmaceutical compositions of the present invention will vary depending upon the age, weight and mammalian species treated, the particular compounds employed, the particular mode of administration and the desired effects and the therapeutic indication. Because these factors and their relationship to determining this amount are well known in the medical arts, the determination of therapeutically effective dosage levels, the amount necessary to achieve the desired result of ameliorating the effects caused by the hemorrhagic fever will be within the ambit of one skilled in these arts.

Typically, administration of the compounds or pharmaceutical composition of the present invention is commenced at lower dosage levels, with dosage levels being increased until the desired therapeutic effect is achieved which would define a therapeutically effective amount. For the compounds of the present invention, alone or as part of a pharmaceutical composition, such doses are between about 0.001 mg/kg and 100 mg/kg body weight, preferably between about 0.05 and 10 mg/kg, body weight.

To assist in understanding, the present invention will now be further illustrated by the following examples. These examples as they relate to this invention should not, of course be construed as specifically limiting the invention and such variations of the invention, now known or later developed, which would be within the purview of one skilled in the art are considered to fall within the scope of the invention as described herein and hereinafter claimed.

EXAMPLE 1

Production of Recombinant Nematode-Extracted Anticoagulant Protein c2/Proline (AcaNAPc2/Proline or rNAPc2/Pro)

A. Preparation of rNAPc2/Pro Expression Plasmid and *Pichia pastoris* Expressing Clone The rNAPc2/Pro gene was cloned into the *P. Pastoris* expression vector, pYAM7sp8[1], using PCR rescue. The pYAM7sp8 vector (see, FIG. 1) is a derivative of pHIL-D2[2]. It contains the promoter and transcriptional termination signal of the *Pichia pastoris* AOX1 gene, a secretion signal peptide (a fusion of the *Pichia pastoris* acid phosphatase signal sequence and the pro sequence of a hybrid *S. cerevisiae* α-mating factor), and the HIS4 marker for selecting transfectants.

The PCR primers used to rescue the rNAPc2 gene from the phage clone[3] were:

(SEQ. ID. NO. 1)
A8 ($^5$'GCG TTT AAA GCA ACG ATG CAG TGT GGT G$3'$)

and (SEQ. ID. NO. 2)
A9 ($^5$'C GCT CTA GAA GCT TCA TGG GTT TCG AGT TCC GGG ATA TAT AAA GTC$3'$).

These primers add DraI and XbaI sites to the 5' and 3' ends of the rescued DNA fragment, respectively. Primer A9 also inserts a proline codon just before the termination codon.

FIG. 1 depicts a rNAPc2/Pro *P. pastoris* expression vector.

The resulting PCR fragment was digested with DraI and XbaI and cloned into pYAM7sp8 digested with StuI and SpeI. Ligating the blunt ends of pYAM7sp8 (StuI) and the PCR fragment (DraI) resulted in an in-frame fusion of the *P. pastoris* secretion signal peptide to the mature portion of rNAPc2/Pro. Ligating the XbaI and SpeI ends of the PCR fragment and pYAM7sp8 resulted in the destruction of the pYAM7sp8 SpeI site. The *P. pastoris* expression strain was constructed by integrating the expression cassette into the *P. pastoris* genome by homologous recombination. The pYAM7sp8/NAPc2/Pro construct was digested with NotI. The digested plasmid was electroporated into *P. pastoris* GS115 (his4-) cells. Transfectants were screened for methanol utilization phenotype (mut+) and high-level expression of rNAPc2/Pro. A single isolate (designated as GS115/AcaNAPc2P-55) was selected for generation of the Master Cell Bank (MCB). The production strain was analyzed by Southern blots that were probed by radiolabeled rNAPc2/Pro or HIS4 genes. These blots showed that multiple copies of the expression cassette were integrated at the 3'-site of the AOX1 gene.

i. Master Cell Bank (MCB)

The Master Cell Bank (MCB) was prepared using a prebank of a single colony isolate (GS115/AcaNAPc2P-55). The flask containing YEPD flask medium (bacto peptone, yeast extract, and dextrose) with 2% glucose was inoculated with 0.5 mL of the prebank and grown to an optical density ($A_{550\ nm}$) of 0.5 to 1.0. The culture was harvested, diluted with glycerol to a final concentration of 15% as a cryopreservative, and frozen in cryovials stored below −60° C.

ii. Manufacturer's Working Cell Bank

A Manufacturer's Working Cell Bank (MWCB) was manufactured from a vial of the MCB. A vial of the MCB was used to inoculate a flask containing Yeast Peptone medium (peptone and yeast extract) and 2% dextrose. The flask was incubated at 28±2° C. and 250 rpm until the optical density ($A_{600\ nm}$) was 17.0±5.0. The culture was harvested, and the cryopreservative, glycerol, was added to a final concentration of 9%. Aliquots of 1.1±0.1 mL were filled into 2.0 mL cryovials, frozen and stored at −70±10° C.

iii. Test Methods Used for Analysis of Master Cell Bank

Host Identification: The rNAPc2/Pro cell bank culture was streaked onto Trypticase Soy Agar (TSA) plates and the plates were incubated for growth. The isolate was set up for identification using the Vitek® identification system which utilizes a temperature controlled chamber and photometric sensor unit to monitor changes in turbidity of the isolate suspension which has been inoculated into a Vitek® yeast test card containing substrates for 26 conventional biochemical tests. For the rNAPc2/Pro cell bank host identifications, the resulting reaction biopattern was compared to a positive control organism (*Pichia pastoris*, ATCC No. 76273) reaction biopattern.

Viable Cell Concentration: Viable cell concentration of the rNAPc2/Pro cell bank was measured by enumeration of viable colony forming units (CFU) by preparation of serial dilutions from three cell bank vials (one each from beginning, middle, and end). The dilutions were plated in triplicate onto TSA plates and incubated CFUs are counted and calculations performed to determine cell concentration as CFU/mL.

Structural Gene Sequence Analysis: The cell bank culture was prepared for gene sequencing by amplifying the rNAPc2/Pro gene incorporated into the host genome using the Polymerase Chain Reaction (PCR) technique. The PCR product was purified and the concentration determined. The PCR product was then sequenced using dideoxy chain termination (Sanger) method. The resulting gene sequence of the cell bank was compared to the known DNA sequence of rNAPc2/Pro. Identity was confirmed by a 100% match.

Non-Host Contamination Assay: The rNAPc2/Pro fermentation broth was tested for non-host contamination by inoculating 100 mL onto each of nine TSA plates. Three plates were incubated at three temperatures (20 to 25° C., 30 to 34° C., and 35 to 39° C.). During the seven day incubation period the plates were inspected for microbial colonies that differ from the characteristic host, particularly noting differences in colony morphology, color and/or colony size. A Gram stain was also performed on the final read plate. Appropriate negative controls were included in the assay.

iv. Test Methods Used for Analysis of Manufacturer's Working Cell Bank

Host Identification: The rNAPc2/Pro cell bank culture was streaked onto Sabouraud Dextrose Agar (SDA) plates and the plates were incubated for growth at 20 to 25° C. for 7 days. In parallel, a positive control (ATCC strain of *K. pastoris*, an alternate name for *P. pastoris*) was streaked onto SDA plates in the same manner. Selected colonies that grew were then tested by gram staining.

After the incubation, at least two morphologically similar colonies from each SDA plate were selected from the test sample SDA plates and positive control SDA plates. These colonies were subcultured onto separate SDA plates and incubated at 20 to 25° C. for 7 days. The API 20C AUX test and Gram staining was then performed on growth from each subculture plate. The API test system (bioMérieux SA; Marcy l'Etoile, France) was a manual microbial identification test that contained 20 miniature biochemical tests. The 20C AUX test strip contained 20 biochemical tests specific for identification of yeast. The API testing results for the rNAPc2/Pro cell bank test sample were compared to the results obtained for the positive control to confirm identification.

Viable Cell Concentration: Viable cell concentration of the rNAPc2/Pro cell bank was measured by enumeration of viable colony forming units (CFUs) by preparation of serial dilutions from two cell bank vials, one vial pulled before freezing the bank and one vial pulled after the bank was frozen. A 100 µL aliquot of each dilution was plated onto duplicate TSA and incubated for 5 to 7 days. All plates with countable colonies (30 to 300 CFUs) were counted. Counts obtained from plates of the same test sample dilution were averaged, multiplied by that dilution and divided by the 100 µL aliquot size to report results as CFU/mL.

DNA Sequencing: Total DNA was isolated from the newly created cell bank (test article). The NAPc2/Pro gene was amplified by polymerase chain reaction (PCR) using primers homologous to the 5' and 3' sequences of the cloned NAPc2/Pro gene. The resulting DNA fragment (approximately 500 bp) was purified using standard methods and used as a template for DNA sequencing using a primer walking strategy performed using the Thermo Sequenase radiolabeled terminator cycle sequencing kit (Amersham Biosciences, Piscataway, N.J.). The sequencing films were read by digitization and the sequence data was assembled and analyzed using Sequencher™ software, version 3.0 (Gene Codes Corp., Ann Arbor, Mich.). The consensus sequence produced from the test article was then compared to the theoretical sequence for the NAPc2/Pro gene.

Non-host Contamination: Prior to freezing the newly created cell bank (test article), a vial was submitted for non-host testing. A sample of the broth was diluted one-thousand fold in saline. Duplicate plates of nine different media types were inoculated with 100 µL of the diluted test sample. In addition, a positive control (ATCC strain of *K. pastoris*, an alternate name for *P. pastoris*) was diluted and inoculated onto plates in the same manner. Another set of plates was not inoculated and designated as the negative controls plates. All plates except SDA were incubated at 30 to 35° C. for 48 to 72 hours; the SDA plates were incubated at 20 to 25° C. for 7 days. The plates were examined for growth after 1, and 2 or 3 days. In addition, the SDA plates were examined for growth after 7 days. Any aberrant colonies were identified by API testing and Gram stain.

After day 2 or 3, at least two morphologically similar colonies from each TSA plate were selected from the test sample TSA plates and positive control TSA plates. These colonies were subcultured onto separate TSA plates and incubated at 30 to 35° C. for 48 to 72 hours. The API 20C AUX test and gram staining was then performed on growth from each subculture plate. The API test system (BioMérieux SA; Marcy l'Etoile, France) was a manual microbial identification test that contained 20 miniature biochemical tests. The 20C AUX test strip contained 20 biochemical tests specific for identification of yeast. The API testing results for the test article were compared to the results obtained for the positive control to confirm identification.

B. Production of rNAPc2/Pro

The production of the rNAPc2/Pro consists of fermentation, recovery, purification, bulk filtration and fill. The following sections describe the individual unit operations for each stage of the process.

This section describes the fermentation procedures for production of rNAPc2/Pro. The rNAPc2/Pro protein is produced as a secreted protein by *P. pastoris*. The fermentation process for rNAPc2/Pro consists of seed flasks, a seed fermentation, and a production fermentation.

i. Seed Fermentation

The purpose of the seed fermentation is to provide a suitably dense inoculum for the production fermentation. Three vials of the MWCB were thawed and one milliliter was used to aseptically inoculate each of three two-liter baffled shake flasks containing 250 mL of autoclaved medium at a pH of 6.0±0.1 (Table I). The flasks were covered and transferred to an incubator shaker at 250±5 rpm and 28±2° C. The flasks were incubated for a period of 27.5±2.0 hours and until the cell density, as measured by Wet Cell Weight, was ≦30 g/L. Once these two parameters were achieved, the contents of two of the flasks were aseptically transferred into an autoclaved inoculum bottle.

TABLE I

Seed Flask Medium

| Components | Concentration |
|---|---|
| Potassium Phosphate, dibasic | 2.30 g/L |
| Potassium Phosphate, monobasic | 11.8 g/L |
| Glycerol | 10 mL/L |
| Yeast Nitrogen Base without amino acids | 13.4 g/L |
| Biotin | 0.4 mg/L |

The medium for the seed fermentation (Table III) was transferred into a seed fermentor. The medium was steam sterilized, allowed to cool, and the pH was adjusted to 5.0±0.2 with filter-sterilized 28-30% ammonium hydroxide. Filter-sterilized antifoam solution of 5% (v/v) KFO880 in 50% methanol was then added through a septum to a concentration of 0.5 mL/L. When the temperature stabilizes at 28.0±1.0° C., the medium was inoculated with the contents of the seed flask inoculum bottle at a ratio of 2.5%. The culture pH in the fermentor was maintained at 5.0±0.2 with 28-30% ammonium hydroxide. The growth of the fermentation was monitored by measuring the Wet Cell Weight.

TABLE II

PTM4 Trace salts

| Components | Concentration |
| --- | --- |
| Cupric Sulfate, Pentahydrate | 2.0 g/L |
| Sodium Iodide | 0.08 g/L |
| Sodium Molybdate, Dihydrate | 0.2 g/L |
| Zinc Chloride | 7.0 g/L |
| Ferrous Sulfate, Heptahydrate | 22.0 g/L |
| Boric Acid | 0.02 g/L |
| Cobalt Chloride, Hexahydrate | 0.5 g/L |
| Manganese Sulfate, Monohydrate | 3.0 g/L |
| d-Biotin | 0.2 g/L |
| Sulfuric Acid | 1.0 mL/L |

TABLE III

Seed Fermentation Medium

| Components | Concentration |
| --- | --- |
| Phosphoric acid, 85% | 8.8 mL/L |
| Calcium Sulfate, Dihydrate | 0.93 g/L |
| Magnesium Sulfate, Heptahydrate | 14.3 g/L |
| Potassium Hydroxide | 4.2 g/L |
| Ammonium Sulfate | 5.0 g/L |
| Potassium Sulfate | 18.2 g/L |
| Glycerol, 100% | 7.9 mL/L |
| PTM4 Trace Salts (see Table II) | 3.0 mL/L |

The fermentation was conducted for 15±2 hours and to a final wet cell weight of ≦20 g/L. A portion of the seed fermentation culture was transferred through a steam-sterilized transfer line into an autoclaved inoculum can. A sample of the final seed fermentation was tested for Non-Host Contamination.

ii. Production Fermentation

The purpose of the production fermentation is to produce high levels of rNAPc2/Pro protein. To achieve this, the culture was grown to a high cell density prior to rNAPc2/Pro gene induction. The medium for the production fermentation (Table IV) was prepared in a production fermentor. These media components were dissolved and mixed with purified water USP and then steam sterilized. The tank was cooled to its initial operating temperature of 28.0±1.0° C. A filter-sterilized antifoam solution of 5% (v/v) KFO880 in 50% methanol was then added. The pH was adjusted to its initial operating range of 5.0±0.3 with filter-sterilized 28-30% ammonium hydroxide. When the initial operating conditions were achieved, the medium was inoculated with the contents of the seed fermentation inoculum can at a ratio of 1 kg inoculum per 10 kg of initially batched medium (pre-inoculation weight). The production fermentation consists of four distinct phases: glycerol batch, glycerol fed-batch, methanol adaptation, and methanol induction. Throughout the fermentation, the dissolved oxygen levels were maintained at approximately 35% by the addition of air at a constant rate and the use of backpressure and variable agitation. If additional oxygen is needed once the maximum agitation is achieved, the air stream is supplemented with oxygen gas. The pH of the culture in the fermentor was maintained with 28 to 30% ammonium hydroxide. The antifoam solution was periodically added to control foaming.

TABLE IV

Production Fermentation Medium

| Components | Concentration |
| --- | --- |
| Phosphoric acid, 85% | 8.8 mL/L |
| Calcium Sulfate, Dihydrate | 0.93 g/L |
| Magnesium Sulfate, Heptahydrate | 14.3 g/L |
| Potassium hydroxide | 4.13 g/L |
| Potassium Sulfate | 18.2 g/L |
| Ammonium Sulfate | 5.0 g/L |
| Glycerol, 100% | 23.8 mL/L |
| PTM4 Salts (see Table II) | 3.0 mL/L |

The first phase of the fermentation, the glycerol batch phase, builds biomass. The fermentor was run at 28±2° C. until the glycerol in the media was depleted, as detected by an oxygen spike caused by the cease of metabolism of the glycerol. This was followed by the glycerol fed-batch phase in which a 50% w/w glycerol solution was fed to the culture at 18.0±1.0 mL/kg pre-inoculation weight/hour for a total of 8.5 hours to increase biomass and repress expression. During the first 4.5 hours of this glycerol feed phase, the pH set point of the culture was lowered from 5.0±0.3 to 2.9±0.1 in 0.5 pH units each hour. Temperature was maintained at 28±2° C. throughout this phase. The WCW was ≦225 g/L prior to the end of the glycerol fed-batch phase.

In the methanol adaptation phase, the glycerol feed was terminated and replaced with a methanol feed which induced the organism to produce rNAPc2/Pro. The methanol feed (containing 6.0 mL/L KFO880 antifoam) was started at 3.0 mL/kg pre-inoculation weight/hour. The culture was tested for methanol adaptation beginning at 2 hours after initiating the methanol addition. The test for methanol adaptation consisted of briefly terminating the feed and verifying a spike in dissolved oxygen. After the first four hours of methanol addition the temperature was lowered to 25±1° C. over a 2 hour period. After the first four hours of methanol addition and after verification that the culture was utilizing methanol, the methanol feed rate was increased by 1.0 mL/kg pre-inoculation weight/hour. Methanol consumption was measured hourly to ensure that the methanol was being completely depleted, at which point the methanol feed rate was increased by 1.0 mL/kg pre-inoculation weight/hour, up to a final feeding rate of 6.0 mL/kg pre-inoculation weight/hour.

During the methanol induction phase, the processing conditions at the end of the methanol adaptation phase were maintained throughout the remaining fermentation. Beginning at approximately 48 hours of total fermentation time, the production of rNAPc2/Pro was monitored by determining the concentration of the broth supernatant, as measured by C8 Reversed-Phase assay. The production fermentor was harvested after 144 to 168 hours in the production fermentor, and after the rNAPc2 concentration as measured by the C8 Reversed-Phase assay was ≦0.55 g/L. A sample of the final fermentation was tested for Non-Host Contamination.

C. Purification of rNAPc2/Pro i. Recovery Step

The purpose of the Recovery step is to separate the rNAPc2/Pro from the cell debris and to exchange the product into a buffer suitable for the first purification chromatography step. The medium used to achieve the separation is an expanded bed ion exchange chromatography column of Streamline SP XL resin (Amersham Biosciences). The fermentation broth was diluted with purified water until the conductivity was ≦9 mS/cm. The solution was adjusted to a concentration of 150 mM acetate and the pH was adjusted to pH 3.1±0.2 using 17.4 M acetic acid. The load solution was applied to an expanded resin bed that has been equilibrated with 500 mM sodium acetate, pH 3.2 followed by 50 mM sodium acetate, pH 3.2. The column was washed in upflow mode with 50 mM sodium acetate, pH 3.2 and then with 50 mM sodium acetate/150 mM NaCl, pH 3.2. The resin bed was allowed to settle and an additional wash was performed using the 50 mM sodium acetate/150 mM NaCl, pH 3.2 in downflow mode. rNAPc2/Pro was eluted by the application of 50 mM sodium acetate/350 mM NaCl, pH 3.2 and the rNAPc2/Pro concentration was measured by the C8 Reversed-Phase assay.

In preparation for the Source 15PHE chromatography step, solid sodium sulfate was added to the Streamline eluate to a final concentration of 0.85 M. The pH was adjusted to 3.1±0.2 using 2.4 M citric acid and the conductivity was verified to be 100±10 mS/cm. The conditioned Streamline eluate was filtered through 0.45 μm filters.

Following the Recovery step, the initial purification step partially purifies the product by removing some protein and non-proteinaceous contaminants from rNAPc2/Pro using a column of Source 15PHE hydrophobic interaction chromatography (HIC) media (Amersham Biosciences). The filtered, conditioned Streamline eluate was applied to a Source 15PHE column previously equilibrated with 50 mM sodium citrate/1.1 M sodium sulfate, pH 3.0. After loading, the column was washed with the equilibration buffer. The rNAPc2/Pro protein was eluted from the column using a 15 column volume gradient from 1.1 M to 0.3 M sodium sulfate in 50 mM sodium citrate, pH 3.0, followed by a gradient hold of the 0.3 M sodium sulfate until the UV absorbance returned to baseline. Fractions were collected across the rNAPc2/Pro elution peak and then analyzed by the C18 Reversed-Phase assay. Those fractions containing a high purity of rNAPc2/Pro were pooled and tested by the Concentration by UV assay. The pH of the Source 15PHE pool was adjusted to pH 5.3±0.1 by the addition of 5N NaOH.

The purpose of ultrafiltration/diafiltration procedure 1 ("UF/DF#1") following the HIC procedure is to concentrate the product and to exchange the rNAPc2/Pro into the buffer used for the Source 15Q (HIC) chromatography. Regenerated cellulose ultrafiltration filters of a 3 kD molecular weight pore size were utilized. The pH-adjusted Source 15PHE pool was concentrated to 2.0±0.5 g/L (as measured by Concentration by UV) on the membranes of UF/DF#1 that were previously equilibrated with 50 mM sodium acetate, pH 5.3. The pool was then diafiltered with ≦5 volumes of 50 mM sodium acetate, pH 5.3, and until the pH was 5.3±0.1 and the conductivity was ≦6.0 mS/cm. The diafiltered UF/DF#1 pool was filtered through a 0.2 μm filter in preparation for loading onto the Source 15Q column.

The final chromatography unit operation ("Final UF/DF") removed most of the remaining protein and non-proteinaceous contaminants from rNAPc2/Pro using a column of Source 15Q ion exchange chromatography media (Amersham Biosciences). The filtered UF/DF#1 pool was applied to the Source 15Q chromatography column previously equilibrated with 500 mM sodium acetate, pH 5.3 followed by 50 mM sodium acetate, pH 5.3. After loading, the column was washed with the 50 mM sodium acetate, pH 5.3 equilibration buffer. A 20 column volume linear gradient from 0 to 400 mM NaCl in 50 mM sodium acetate, pH 5.3 was applied to the column. Fractions are collected across the elution peak and analyzed by the C18 Reversed-Phase assay. Those fractions of high rNAPc2/Pro purity were pooled and tested by the Concentration by UV assay.

The purpose of the Final UF/DF is to concentrate the product and to exchange the rNAPc2/Pro into the final formulation buffer. Regenerated cellulose ultrafiltration filters of a 3 kD molecular weight pore size are utilized. The Source 15Q pool was concentrated to 12.0±0.5 g/L (as measured by Concentration by UV) on the Final UF/DF membranes that have been previously equilibrated with the final formulation buffer, 65 mM sodium phosphate/80 mM sodium chloride, pH 7.0. The pool was then diafiltered with ≦6 volumes of the formulation buffer, and until the pH was 7.0±0.1.

The purified rNAPc2/Pro was transferred into a Class 100 area and filtered using a Millipak 0.2 μm filter into autoclaved 1 liter molded Nalgene Tefzel® FEP (fluorinated ethylene propylene) 1600 series bottle with a molded, linerless, non-contaminating Tefzel®ETFE (ethylene tetrafluoroethylene copolymer) screw closure. The bottles were transferred into a −20±10° C. freezer for storage. This material may be formulated using either the standard liquid or lyophilized formations suitable for treating patients.

ii. Description of rNAPc2/Pro In-Process Test Methods a. Wet Cell Weight

Approximately 1.5 mL of fermentation samples were added to tared microcentifuge tubes and centrifuged at 10,000 rpm for approximately 5 minutes. The supernatant from each tube was decanted and the tubes containing the solids were weighed. The wet cell weight is equal to the net weight divided by the original sample volume.

b. Non-Host Contamination Assay

The final broth of the seed and production fermentation samples were tested for non-host contamination by inoculating 100 μL onto each of nine TSA plates. Three plates were incubated at three temperatures (20 to 25° C., 30 to 34° C. and 35 to 39° C.). During the seven day incubation period the plates were inspected for microbial colonies that differ from the characteristic host, particularly noting differences in colony morphology, color and/or colony size. A Gram stain was also performed on the final read date. Appropriate negative controls were included in the assay.

c. C8 Reversed-Phase Assay (Concentration and Purity)

The supernatants of the production fermentation samples, and Streamline SP XL samples were 0.22 μm filtered and then injected onto a Kromasil C8, 4.6×250 mm Reversed-Phase column. The column was equilibrated with 22% acetonitrile, 0.1% trifluoroacetic acid (TFA) prior to the sample injection. A linear gradient was then run from 22-28% acetonitrile in 0.1% TFA over twenty minutes at 1 mL/min to elute the rNAPc2/Pro material. rNAPc2/Pro standard dilutions of known concentrations were used to generate a standard curve based upon a linear regression of rNAPc2/Pro mg/mL versus peak area. The amount of rNAPc2/Pro in any sample is extrapolated from the standard curve and divided by the volume of sample injected to determine the concentration of rNAPc2/Pro in the samples. rNAPc2/Pro purity is calculated as a percent of the total peak area.

d. Concentration by UV

The concentration of each purification pool from the Source 15PHE through the UF/DF-Final was determined using its absorbance at 280 nm on a suitably calibrated spectrophotometer. The instrument was blanked using the applicable buffer solution prior to running the test samples. Test samples were prepared in triplicate by diluting within the linear range (between 0.13 to 1.62 AU). The average absorbance at 280 nm was divided by the extinction coefficient [0.59 AU*cm$^{-1}$*(mg/mL)$^{-1}$] and multiplied by the dilution factor to obtain the concentration in mg/mL.

e. C18 Reversed-Phase Assay (Purity)

The purity of the Source 15PHE fractions and pool, UF/DF #1 pool, Source 15Q fractions and pool, and the Final UF/DF pool were each analyzed by the C18 Reversed-Phase assay. rNAPc2/Pro was separated from other components of a sample by linear gradient Reversed-Phase chromatography. Samples were diluted, if necessary, to approximately 1 mg/mL in cPBS and 30 μL was injected into a Waters Symmetry C18 Reversed-Phase column (5 μm particles, 4.6 mm I.D.×250 mm length) equilibrated in 78% mobile phase A (0.1% TFA in water) and 22% mobile phase B (0.1% TFA in acetonitrile). The percentage of mobile phase B was then increased linearly to 26% over a twenty minute time period, using a 1 mL/min flow rate. The peaks were monitored by the UV detector at 210 nm. The purity of rNAPc2/Pro is calculated by dividing the area of the rNAPc2/Pro peak by the total peak area in the chromatogram and expressing that as a percentage.

iii. Characterization of rNAPc2/Pro

The identity of rNAPc2/Pro was confirmed using amino acid sequence analysis and peptide mapping techniques. The purity of the preparation was judged to be >96% using C18 reverse-phase chromatography.

iv. Bioactivity rNAPc2/Pro prolongs the clotting time of human plasma initiated by the addition of thromboplastin in a concentration-dependent manner. The anticoagulant effect of rNAPc2/Pro on the clotting of human plasma is directly measured in an automated Prothrombin Time (PT) Clotting Assay using rabbit brain thromboplastin (tissue factor, Simplastin-Excel) to initiate clotting.

Both rNAPc2/Pro reference standard and rNAPc2/Pro sample were diluted to 1035 nM in assay buffer. The test instrument (Coag-A-Mate MAX, BioMérieux) then made a set of dilutions in human plasma from the starting preparation and measured the resulting clotting time (CTs) in seconds. Curves were defined by linear regression fit of the log CTs of the rNAPc2/Pro versus the dilution concentrations. The bioactivity of the test article was then calculated as the ratio of the slope of the curve of the test article to the curve of the reference standard times the activity of the reference standard.

REFERENCES

1. Laroche Y, Storme V, De Meutter J, Messens J, Lauwereys M. (1994) Biotechnology 12, 1119-1124.
2. Despreaux C W, Manning R F. (1993) Gene 106, 35-41.
3. Jespers L S, Messens J H, De Keyser A, Eckhout E, Van Den Brande I, Gansemans Y G, Lauwereys M J, Vlasuk G P, Stanssens P E. (1995) Biotechnology 13, 378-382.

EXAMPLE 2

Evaluation of Factor VIIa/Tissue Factor (fVIIa/TF) Inhibitor in a Non-Human Primate Model of Acute-Infection with Ebola Virus (EBOV).

Filovirus-naïve rhesus macaques (*Macaca mulatta*) were randomized into one experimental group consisting of four monkeys (three females, one male), and one control group consisting of one animal (male). All animals were exposed to 1000 plaque forming units (PFU) of EBOV (Zaire subtype) by intramuscular injection following a ≦ one week acclimation to a biosafety level (BSL)-4 animal room located at the United States Army Medical Research Institute of Infectious Diseases (USAMRIID), Fort Detrick, Md. Animals in the experimental group were treated with 30 μg/kilogram body weight (kg) of the test fVIIa/TF inhibitor (rAcaNAPc2/proline) by a single subcutaneous injection within 1 hour after virus challenge, and continuing daily for 14 days after exposure to EBOV. The control animal received an equivalent volume of placebo (a modified phosphate buffered saline excipient (cPBS)) following the same regimen as the treated animals. The daily doses of active drug and placebo were administered by momentarily restraining animals in the cages (i.e., employing the squeeze mechanism). Tissues obtained upon death were prepared and analyzed as described (Giesbert, T. W., et. al. (2002) *Emerging Infectious Diseases* 8:503-507)

Out of the four treated monkeys there was one survivor that remains alive to date (male) and two deaths occurring on days 8, 13, and 14 (all female). The control male animal died on day 9. From previous experience, the incidence of mortality for untreated animals in this model is ~100% with death occurring between 7 to 10 days with the mean being 8.4 days following infection. The first female that died on day 8 started cycling heavily the first day after infection and appeared to succumb from bleeding due to cycling that was possibly exacerbated by the treatment drug. The two other female animals also cycled early in the disease course however, the time to death was prolonged. The animal that died on day 13 had low viremia and virus in tissues, (i.e., appeared to be clearing the infection). The hematocrit on this animal was 8.4 when it was euthanized. The animal that died on day 14 had a platelet count of 219 on day 13 but also appeared to be anemic. It has been proposed that that at least one of the treated females and possibly all three could have been saved with a blood transfusion since it did not appear that the animals succumbed to normal disease pathogenesis expected after EBOV infection based on histopathological examination. The lone treated male remains alive to date. This animal clearly had infection based on the titer of EBOV antibodies, a significant drop in platelets from a count of 330 pre-infection to 53 on day 10, post infarction and a loss of appetite.

An additional experiment was performed in which three male animals were infected with Ebola virus and treated with rAcaNAPc2/Pro as described above. An additional male was used as a control and did not receive rAcaNAPc2/Pro following infection. In this experiment, one animal in the treated group was found to have underlying case of shigellosis and was not included in the analysis. Out of the two other animals, there was one who survived and is alive to date and one animal that died on day 10 post infection. The control animal died on day 9 post infection. The animal that died on day 10 showed signs of recovery and upon necropsy and histopathological examination the internal organs did not resemble the virus control. The survivor in this study as well as that in the previous study have high titer anti-Ebola antibodies, indicating that each animal was exposed to Ebola virus.

In summary, the results from two independent experiments demonstrate that rAcaNAPc2/Pro provided complete protection and a survival benefit to 2 out of 6 (33%), delayed mortality in 3 out of the 6 (50%) and no benefit in 1 out of 6 (17%) animals infected with Ebola and administered rAcaNAPc2/pro. Two out of two (100%) of the control animals not receiving rAcaNAPc2/pro died. Therefore, rNAPc2/Pro has demonstrated significant utility in a non-human primate model of Ebola virus infection that is considered the only model that, at present, is considered to reflect the same physiological and clinical characteristics of Ebola virus infection in humans (Geisbert et al. "Evaluation in nonhuman primates of vaccines against Ebola virus". Emerging Infectious Diseases (2002) 8:503-507; Schou et al, "Marburg and Ebola virus infections in laboratory non-human primates: a literature review", Comparative Medicine (2000) 50:108-123).

EXAMPLE 3

Assays for Measuring the Inhibition of the fVIIa/TF Complex by a Test Compound

A. fVIIa/TF fIX Activation Assay

This example measures the ability of a test compound to act as an inhibitor of the catalytic complex of fVIIa/TF, which has a primary role in initiation of the coagulation response in the ex vivo prothrombin time assay (Example 5). Activation of tritiated Factor IX by the rFVIIa/rTF/PLV complex was assessed by determining the respective intrinsic inhibition constant, $K_i^*$.

Lyphilized, purified, recombinant human factor VIIa was obtained from BioPacific, Inc. (Emeryville, Calif.), and reconstituted in HBS (10 mM HEPES, pH 7.5, 150 mM sodium chloride) prior to use. Purified human Factor X was obtained from Enzyme Research Laboratories, Inc. (South Bend, Ind.) and Factor Xa (free FXa) was activated and prepared from it as described (Bock, P. E., Craig, P. A., Olson, S. T., and Singh, P. Arch. Biochem. Biophys. 273: 375-388 (1989)). Active site-blocked human Factor Xa (EGR-FXa), which had been irreversibly inactivated with L-Glutamyl-L-glycyl-L-arginyl chloromethylketone, was obtained from Haematologic Technologies, Inc. (Essex Junction, Vt.). Recombinant human tissue factor (rTF) was produced by a baculovirus-expression system, and purified to homogeneity by monoclonal antibody affinity chromatography (Corvas International, Inc., San Diego, Calif.).

The purified rTF apoprotein was incorporated into phospholipid vesicles (rTF/PLV), consisting of phosphotidyl choline (75%, w/v) and phosphotidyl serine (25%, w/v) in the presence of detergent, as described by Ruf et al. (Ruf, W., Miles, D. J., Rehemtulla, A., and Edgington, T. S. Methods in Enzymology 222: 209-224 (1993)). The phospholipids were purchased from Avanti Polar Lipids, (Alabaster, Ala.). The buffer used for all assays was HBSA, HBS containing 0.1% (w/v) bovine serum albumin. All reagents were obtained from Sigma Chemical Co. (St. Louis, Mo.), unless otherwise indicated.

The activation of human $^3$H-Factor IX (FIX) by the rFVIIa/TF complex was monitored by measuring the release of the radiolabeled activation peptide. Purified human fIX was obtained from Haematoligic Technologies, Inc. (Essex Junction, Vt.), and radioactively labeled by reductive tritiation as described (Van Lenten & Ashwell, 1971, JBC 246, 1889-1894). The resulting tritiated preparation of FIX had a specific activity of 194 clotting units/mg as measured in immuno-depleted FIX deficient plasma (Ortho), and retained 97% of its activity. The radiospecific activity was $2.7 \times 10^8$ dpm/mg. The Km for the activation of $^3$H-FIX by rFVIIa/rTF/PLV was 25 nM, which was equivalent to the Km obtained for untreated (unlabeled) FIX.

The assay for $K_i^*$ determinations was conducted as follows: rFVIIa and rTF/PLV were combined in a polypropylene test tube, and allowed to form a complex for 10 minutes in HBSA, containing 5 mM $CaCl_2$. Aliquots of rFVIIa/rTF/PLV complex were combined in the appropriate polypropylene microcentrifuge tubes with EGR-FXa or free FXa, when included, and either the test compound at various concentrations, after dilution into HBSA, or HBSA alone (as $V_o$ (uninhibited velocity) control). Following an incubation of 60 minutes at ambient temperature, reactions were initiated by the addition of $^3$H-FIX. The final concentration of the reactants in 420 µl of HBSA was: rFVIIa (50 pM), rTF (2.7 nM), PLV (6.4 micromolar), either EGR-FXa or free FXa (300 pM), recombinant AcaNAPc2 (5 to 1,500 pM), $^3$H-FIX (200 nM), and $CaCl_2$ (5 mM). In addition, a background control reaction was run that included all of the above reactants, except rFVIIa.

At specific time points (8, 16, 24, 32 and 40 minutes), 80 µl of the reaction mixture was added to an eppendorf tube that contained an equal volume of 50 mM EDTA in HBS with 0.5% BSA to stop the reaction; this was followed by the addition of 160 µl of 6% (w/v) trichloroacetic acid. The protein was precipitated, and separated from the supernatant by centrifugation at 16,000×g for 6 minutes at 4° C. The radioactivity contained in the resulting supernatant was measured by removing triplicate aliquots that were added to Scintiverse BD (Fisher Scientific, Fairlawn, N.J.), and quantitated by liquid scintillation counting. The control rate of activation was determined by linear regression analysis of the soluble counts released over time under steady-state conditions, where less than 5% of the tritiated FIX was consumed. The background control ($\leq 1.0\%$ of control velocity) was subtracted from all samples. Ratios of inhibited pre-equilibrium, steady-state velocities (Vi), containing either test compound to the uninhibited control velocity of rFVIIa/TF alone ($V_o$) were plotted against the corresponding concentrations of test compound. These data were then directly fit to an equation for tight-binding inhibitors (Morrison, J. F., and Walsh, C. T., Adv. Enzymol. 61:201-300 (1988)), from which the apparent equilibrium dissociation inhibitory constant $K_i^*$ was calculated.

The data for rAcaNAPc2 is presented in Table V which follows Section B, below.

B. Factor VIIa/Tissue Factor Amidolytic Assay

The ability of a test compound to act as an inhibitor of the amidolytic activity of the fVIIa/TF complex was assessed by determining the respective inhibition constant, $K_i^*$, in the presence and absence of active site-blocked human Factor Xa (EGR-fXa).

rFVIIa/rTF amidolytic activity was determined using the chromogenic substrate S-2288 (H-D-isoleucyl-L-prolyl-L-arginine-p-nitroaniline), obtained from Kabi Pharmacia Hepar, Inc. (Franklin, Ohio). The substrate was reconstituted in deionized water prior to use. rFVIIa and rTF/PLV were combined in a polypropylene test tube, and allowed to form a complex for 10 minutes in HBSA, containing 3 mM $CaCl_2$. The assay for $K_i^*$ determinations was conducted by combining in appropriate wells of a Corning microtiter plate 50 µl of the rFVIIa/rTF/PLV complex, 50 µl of EGR-FXa and 50 µl of either the test compound at various concentrations, after dilution into HBSA, or HBSA alone (for $V_o$ (uninhibited velocity) measurement). Following an incubation of 30 minutes at ambient temperature, the triplicate reactions were initiated by adding 50 µl of S-2288. The final concentration of reactants in total volume of 200 µl of HBSA was: test compound NAP (0.025 to 25 nM), rFVIIa (750 pM), rTF (3.0 nM), PLV (6.4 micromolar), EGR-FXa (2.5 nM), and S-2288 (3.0 mM, 3× Km).

The amidolytic activity of rFVIIa/rTF/PLV was measured as a linear increase in the absorbance at 405 nm over 10 minutes (velocity), using a Thermo Max® Kinetic Microplate Reader (Molecular Devices, Palo Alto, Calif.), under steady-state conditions, where less than 5% of the substrate was consumed. Ratios of inhibited pre-equilibrium, steady-state velocities (Vi), containing test compound to the uninhibited velocity of free fXa alone ($V_o$) were plotted against the corresponding concentrations of test compound. These data were then directly fit to the same equation for tight-binding inhibitors, used in Example 3A, from which the apparent equilibrium dissociation inhibitory constant $K_i^*$ was calculated.

TABLE V

| Test Compound | Ki* (pM) | | | | |
|---|---|---|---|---|---|
| | Amidolytic Assay | | $^3$H-FIX Activation | | |
| | No Addition | Plus EGR-FXa | No Addition | +free FXa | +EGR-FXa |
| AcaNAP2[a] | NI | 36 ± 20 | NI | 35 ± 5 | 8.4 ± 1.5 |

NI = no inhibition
ND = not determined
[a]Made in *Pichia pastoris*. (See, U.S. Pat. No. 5,866,542.)

EXAMPLE 4

Factor Xa Amidolytic Assay

The ability of a test compound to act as an inhibitor of factor Xa catalytic activity was assessed by determining the test compound-induced inhibition of amidolytic activity catalyzed by the human enzyme, as represented by $K_i^*$ values.

The buffer used for all assays was HBSA (10 mM HEPES, pH 7.5, 150 mM sodium chloride, 0.1% bovine serum albumin). All reagents were from Sigma Chemical Co. (St. Louis, Mo.), unless otherwise indicated.

The assay was conducted by combining in appropriate wells of a Corning microtiter plate, 50 microliters of HBSA, 50 microliters of the test compound diluted (0.025 to 35 nM) in HBSA (or HBSA alone for uninhibited velocity measurement), and 50 microliters of the Factor Xa enzyme diluted in HBSA (prepared from purified human Factor X obtained from Enzyme Research Laboratories (South Bend, Ind.) according to the method described by Bock, P. E. et al., Archives of Biocyhem, Biophys. 273: 375 (1989). The enzyme was diluted into HBSA prior to the assay in which the final concentration was 0.5 nM). Following a 30 minute incubation at ambient temperature, 50 microliters of the substrate S2765 (N-alpha-benzyloxycarbonyl-D-argininyl-L-glycyl-L-arginine-p-nitroanilide dihydrochloride, obtained from Kabi Diagnostica (or Kabi Pharmacia Hepar Inc., Franklin, Ohio) and made up in deionized water followed by dilution in HBSA prior to the assay) was added to the wells yielding a final total volume of 200 microliters and a final concentration of 250 micromolar (about 5-times Km). The initial velocity of chromogenic substrate hydrolysis was measured by the change in absorbance at 405 nm using a Thermo Max® Kinetic Microplate Reader (Molecular Devices, Palo Alto, Calif.) over a 5 minute period in which less than 5% of the added substrate was utilized.

Ratios of inhibited pre-equilibrium, steady-state velocities containing test compound (Vi) to the uninhibited velocity of free fXa alone ($V_o$) were plotted against the corresponding concentrations of test compound. These data were then directly fit to an equation for tight-binding inhibitors (Morrison, J. F., and Walsh, C. T., Adv. Enzymol. 61:201-300 (1988)), from which the apparent equilibrium dissociation inhibitory constant $K_i^*$ was calculated.

Table VI below gives the Ki* values for the test compound AcaNAPc2 (SEQ. ID. NO. 59). The data show that AcaNAPc2 did not effectively inhibit FXa amidolytic activity.

TABLE VI

| Compound | Ki* (pM) |
|---|---|
| AcaNAPc2[a] | NI* |

*NI = no inhibition; a maximum of 15% Inhibition was observed up to 1 μM.
[a]Made in *Pichia pastoris*. (See, U.S. Pat. No. 5,866,542.)

EXAMPLE 5

Prothrombin Time (PT) and Activated Partial Thromboplastin Time (aPTT) Assays

The ex vivo anticoagulant effects of a test compound was evaluated by measuring the prolongation of the activated partial thromboplastin time (aPTT) and prothrombin time (PT) over a broad concentration range of the test compound.

Fresh frozen pooled normal citrated human plasma was obtained from George King Biomedical, Overland Park, Kans. Respective measurements of aPTT and PT were made using the Coag-A-Mate RA4 automated coagulometer (General Diagnostics, Organon Technica, Oklahoma City, Okla.) using the Automated aPTT PlatelinO L reagent (Organon Technica, Durham, N.C.) and Simplastin® Excel (Organon Technica, Durham, N.C.) respectively, as initiators of clotting according to the manufacturer's instructions.

The assay was conducted by making a series of dilutions of test compound in rapidly thawed plasma followed by adding 200 microliters or 100 microliters to the wells of the assay carousel for the aPTT or PT measurements, respectively. Alternatively, the test compound was serially diluted into HBSA and 10 μl of each dilution were added to 100 μl of normal human plasma in the wells of the Coag-A-Mate assay carousel.

Concentrations of test compound were plotted against clotting time, and a doubling time concentration was calculated, i.e., a specified concentration of test compound that doubled the control clotting time of either of the PT or the aPTT. The control clotting times of NHP in the PT and APTT were 12.1 seconds and 28.5 seconds, respectively.

Table VII below shows the ex vivo anticoagulant effects of AcaNAPc2 (SEQ. ID. NO. 3), represented by the concentration of that doubled (doubling concentration) the control clotting time of normal human plasma in the respective PT and APTT clotting assays relative to a control assay where no test compound was present. The data show the activity of the test compounds as an anticoagulant of clotting human plasma.

TABLE VII

| Compound | Doubling Concentration (nM) in the PT | Doubling Concentration (nM) in the aPTT |
|---|---|---|
| AcaNApc2[a] | 15 ± 1 | 105 ± 11 |

[a]Made in *Pichia pastoris*. (See, U.S. Pat. No. 5,866,542.)

EXAMPLE 6

Prothrombinase Inhibition Assay

The ability of a test compound to act as an inhibitor of the activation of prothrombin by Factor Xa that has been assembled into a physiologic prothrombinase complex was assessed by determining the respective inhibition constant, $K_i^*$.

Prothrombinase activity was measured using a coupled amidolytic assay, where a preformed complex of human FXa, human Factor Va (FVa), and phospholipid vesicles first activates human prothrombin to thrombin. The amidolytic activity of the generated thrombin is measured simultaneously using a chromogenic substrate. Purified human FVa was obtained from Haematologic Technologies, Inc. (Essex Junction, Vt.). Purified human prothrombin was purchased from Celsus Laboratories, Inc. (Cincinnati, Ohio). The chromogenic substrate Pefachrome t-PA ($CH_3SO_2$-D-hexahydrotyrosine-glycyl-L-arginine-p-nitroanilide) from Pentapharm Ltd (Basel, Switzerland) was purchased from Centerchem, Inc. (Tarrytown, N.Y.). The substrate was reconstituted in deionized water prior to use. Phospholipid vesicles were made, consisting of phosphotidyl choline (67%, w/v), phosphatidyl glycerol (16%, w/v), phosphatidyl ethanolamine (10%, w/v), and phosphatidyl serine (7% w/v) in the presence of detergent, as described by Ruf et al. (Ruf, W., Miles, D. J., Rehemtulla, A., and Edgington, T. S. Methods in Enzymology 222: 209-224 (1993)). The phospholipids were purchased from Avanti Polar Lipids, (Alabaster, Ala.).

The prothrombinase complex was formed in a polypropylene test tube by combining FVa, FXa, and phospholipid vesicles (PLV) in HBSA containing 3 mM $CaCl_2$ for 10 minutes. In appropriate wells of a microtiter plate, 50 µl of test compound diluted in HBSA, or HBSA alone (for $V_o$ (uninhibited velocity) measurement). Following an incubation of 30 minutes at room temperature, the triplicate reactions were initiated by the addition of a substrate solution, containing human prothrombin and the chromogenic substrate for thrombin, Pefachrome tPA. The final concentration of reactants in a total volume of 150 µl of HBSA was: test compound (0.025 to 25 nM), FXa (250 µM), PLV (5 µM), prothrombin (250 nM), Pefachrome tPA (250 µM, 5× Km), and $CaCl_2$ (3 mM).

The prothrombinase activity of fXa was measured as an increase in the absorbance at 405 nm over 10 minutes (velocity), exactly as described in Example 4, under steady-state conditions. The absorbance increase was sigmoidal over time, reflecting the coupled reactions of the activation of prothrombin by the FXa-containing prothrombinase complex, and the subsequent hydrolysis of Pefachrome tPA by the generated thrombin. The data from each well of a triplicate were combined and fit by reiterative, linear least squares regression analysis, as a function of absorbance versus time$^2$, as described (Carson, S. D. Comput. Prog. Biomed. 19: 151-157 (1985)) to determine the initial velocity ($V_i$) of prothrombin activation. Ratios of inhibited steady-state initial velocities containing test compound ($V_i$) to the uninhibited velocity of prothrombinase fXa alone ($V_o$) were plotted against the corresponding concentrations of test compound. These data were directly fit to the equation for tight-binding inhibitors, as in Example 4 above, and the apparent equilibrium dissociation inhibitory constant $K_i^*$ was calculated.

Table VIII below gives the dissociation inhibitor constant ($K_i^*$) of recombinant AcaNAPc2 (SEQ. ID. NO. 59) (made in *Pichia pastoris*) against he activation of prothrombin by human fXa incorporated into a prothrombinase complex.

TABLE VIII

| Compound | $K_i^*$ (pM) |
|---|---|
| AcaNAPc2[a] | 2.385 ± 283 |

[a]Made in *Pichia pastoris*. (See, U.S. Pat. No. 5,866,542.)

The data presented in Examples 4, 5 and 6 suggest that AcaNAPc2 appears to be interacting with FXa in a way that only perturbs the macromolecular interactions of this enzyme with either the substrate and/or cofactor (Factor Va), while not directly inhibiting the catalytic turnover of the peptidyl substrate.

EXAMPLE 7

In vitro Enzyme Assays for Active Specificity Determination

The ability of a test compound to act as a selective inhibitor of fXa catalytic activity or TF/VIIa activity was assessed by determining whether the test compound would inhibit other enzymes in an assay at a concentration that was 100-fold higher than the concentration of the following related serine proteases: thrombin, Factor Xa, Factor XIa, Factor XIIa, kallikrein, activated protein C, plasmin, recombinant tissue plasminogen activator (rt-PA), urokinase, chymotrypsin, trypsin.

A. General Protocol for Enzyme Inhibition Assays

The buffer used for all assays was HBSA (see, Example 4). All substrates were reconstituted in dionized water, followed by dilution into HBSA prior to the assay. The amidolytic assay for determining the specificity of inhibition of serine proteases was conducted by combining in appropriate wells of a Corning microtiter plate, 50 µl of HBSA, 50 µl of test compound at a specified concentration diluted in HBSA, or HBSA alone (uninhibited control velocity, $V_o$), and 50 µl of a specified enzyme (see specific enzymes below). Following a 30 minute incubation at ambient temperature, 50 µl of substrate were added to triplicate wells. The final concentration of reactants in a total volume of 200 µl of HBSA was: test compound (75 nM), enzyme (750 pM), and chromogenic substrate (as indicated below). The initial velocity of chromogenic substrate hydrolysis was measured as a change in absorbance at 405 nm over a 5 minute period, in which less than 5% of the added substrate was hydrolyzed. The velocities of test samples, containing test compound ($V_i$) were then expressed as a percent of the uninhibited control velocity ($V_o$) by the following formula: $V_i/V_o \times 100$, for each of the enzymes.

B. Specific Enzyme Assays i. Thrombin Assay

Thrombin catalytic activity was determined using the chromogenic substrate Pefachrome t-PA ($CH_3SO_2$-D-hexahydrotyrosine-glycyl-L-arginine-p-nitroaniline, obtained from Pentapharm Ltd., Basel, Switzerland). The final concentration of Pefachrom t-PA was 250 µM (about 5-times Km). Purified human alpha-thrombin was obtained from Enzyme Research Laboratories, Inc. (South Bend, Ind.).

ii. Factor Xa Assay

Factor Xa catalytic activity was determined using the chromogenic substrate S-2765 (N-benzyloxycarbonyl-D-arginine-L-glycine-L-arginine-p-nitroaniline), obtained from Kabi Pharmacia Hepar, Inc. (Franklin, Ohio). All substrates were reconstituted in deionized water prior to use. The final concentration of S-2765 was 250 µM (about 5-times Km). Purified human Factor X was obtained from Enzyme Research Laboratories, Inc. (South Bend, Ind.) and Factor Xa (FXa) was activated and prepared from it as described (Bock, P. E., Craig, P. A., Olson, S. T., and Singh, P. Arch. Biochem. Biophys. 273:375-388 (1989)).

iii. Factor XIa Assay

Factor FXIa catalytic activity was determined using the chromogenic substrate S-2366 (L-Pryoglutamyl-L-prolyl-L-arginine-p-nitroaniline, obtained from Kabi Pharmacia Hepar, Franklin, Ohio). The final concentration of S-2366 was 750 µM. Purified human FXIa was obtained from Enzyme Research Laboratories, Inc. (South Bend, Ind.).

iv. Factor XIIa Assay

Factor FXIIa catalytic activity was determined using the chromogenic substrate Spectrozyme FXIIa (H-D-CHT-L-glycyl-L-arginine-p-nitroaniline, (obtained from American Diagnostica, Greenwich, Conn.). The final concentration of Spectrozyme FXIIa was 100 µM. Purified human FXIIa was obtained from Enzyme Research Laboratories, Inc. (South Bend, Ind.).

v. Kallikrein Assay

Kallikrein catalytic activity was determined using the chromogenic substrate S-2302 (H-D-prolyl-L-phenylalanyl-L-arginine-p-nitroaniline, obtained from Kabi Pharmacia Hepar, Franklin, Ohio). The final concentration of S-2302 was 400 µM. Purified human kallikrein was obtained from Enzyme Research Laboratories, Inc. (South Bend, Ind.).

vi. Activated Protein C (aPC)

Activated Protein C catalytic activity was determined using the chromogenic substrate Spectrozyme PCa (H-D-lysyl-(-Cbo)-L-prolyl-L-arginine-p-nitroaniline) were obtained from American Diagnostica Inc. (Greenwich, Conn.). The final concentration was 400 µM (about 4-times Km). Purified human aPC was obtained from Hematologic Technologies, Inc. (Essex Junction, Vt.).

vii. Plasmin Assay

Plasmin catalytic activity was determined using the chromogenic substrate S-2366 (L-Pyroglutamyl-L-prolyl-L-arginine-p-nitroaniline, obtained from Kabi Pharmacia Hepar, Franklin, Ohio). The final concentration of S-2366 was 300 µM (about 4-times Km). Purified human plasmin was obtained from Enzyme Research Laboratories, Inc. (South Bend, Ind.).

viii. Recombinant Tissue Plasminogen Activator (rt-PA)

rt-PA catalytic activity was determined using the substrate, Pefachrome t-PA (CH$_3$SO$_2$-D-hexahydrotyrosine-glycyl-L-arginine-p-nitroaniline, obtained from Pentapharm Ltd., Basel, Switzerland). The final concentration was 500 µM (about 3-times Km). Human rt-PA (Activase®) was obtained from Genentech, Inc. (So. San Francisco, Calif.).

ix. Urokinase

Urokinase catalytic activity was determined using the substrate S-2444 (L-Proglutamyl-L-glycyl-L-arginine-p-nitroaniline, obtained from Kabi Pharmacia Hepar, Franklin, Ohio). The final concentration of S-2444 was 150 µM (about 7-times Km). Human urokinase (Abbokinase®), purified from cultured human kidney cells, was obtained from Abbott Laboratories (North Chicago, Ill.).

x. Chymotrypsin

Chymotrypsin catalytic activity was determined using the chromogenic substrate, S-2586 (Methoxy-succinyl-L-argininyl-L-prolyl-L-tyrosine-p-nitroaniline, which was obtained from Kabi Pharmacia Hepar, Franklin, Ohio). The final concentration of S-2586 was 100 µM (about 8-times Km). Purified (3×-crystallized; CDI) bovine pancreatic-chymotrypsin was obtained from Worthington Biochemical Corp. (Freehold, N.J.).

xi. Trypsin

Trypsin catalytic activity was determined using the chromogenic substrate S-2222 (N-benzoyl-L-isoleucyl-L-glutamyl-(-methyl ester)-L-arginine-p-nitroaniline, which was obtained from Kabi Pharmacia Hepar, Franklin, Ohio). The final concentration of S-2222 was 300 µM (about 5-times Km). Purified human pancreatic trypsin was obtained from Scripps Laboratories (San Diego, Calif.).

xii. Results

Table IX lists the inhibitory effect of recombinant AcaNAPc2 (SEQ. ID. NO. 3) expressed in *Pichis pastoris*, on the amidolytic activity of 11 selected serine proteases. Inhibition is expressed as percent of control velocity. These data demonstrate that AcaNAPc2 possesses a high degree of specificity, and is not a specific inhibitor of FXa.

TABLE IX

| Enzyme | % Control Velocity + AcaNAPc2[a] |
|---|---|
| FXa | 84 ± 3 |
| FIIa | 99 ± 3 |
| FXIa | 103 ± 4 |
| FXIIa | 97 ± 1 |
| kallikrein | 101 ± 1 |
| aPC | 97 ± 3 |
| plasmin | 107 ± 9 |
| r-tPA | 96 ± 2 |
| urokinase | 97 ± 1 |
| chymotrypsin | 99 ± 0 |
| trypsin | 93 ± 4 |

[a]Made in *Pichia pastoris*. (See, U.S. Pat. No. 5,866,542.)

The invention claimed is:

1. A method of treating a mammal having a viral hemorrhagic fever which comprises administering to said mammal an effective amount of a Nematode-Extracted Anticoagulant Protein ("NAP") having Factor VIIa/tissue factor inhibitory activity ("fVIIa/TF"), wherein said NAP comprises one or more NAP domains, wherein each NAP domain includes the sequence: Cys-A1-Cys-A2-Cys-A3-Cys-A4-Cys-A5-Cys-A6-Cys-A7-Cys-A8-Cys-A9-Cys-A10, wherein (a) A1 is an amino acid sequence of 7 to 8 amino acid residues;
(b) A2 is an amino acid sequence of 3 to 5 amino acid residues;
(c) A3 is an amino acid sequence of 3 amino acid residues;
(d) A4 is an amino acid sequence of 6 to 19 amino acid residues;
(e) A5 is an amino acid sequence of 3 to 4 amino acid residues;
(f) A6 is an amino acid sequence of 3 to 5 amino acid residues;
(g) A7 is an amino acid;
(h) A8 is an amino acid sequence of 11 to 12 amino acid residues;
(i) A9 is an amino acid sequence of 5 to 7 amino acid residues; and
(j) A10 is an amino acid sequence of 5 to 25 amino acid residues.

2. A method according to claim 1 wherein said virus is selected from the group consisting of Filoviridae, Arenaviridae, Bunyaviridae and Flaviridae.

3. A method according to claim 2 wherein said virus is from the family Filoviridae.

4. A method according to claim 3 wherein said NAP is AcaNAPc2 (SEQ ID NO:3) and said virus is Marburg virus.

5. A method according to claim 3 wherein said NAP is AcaNAPc2/proline (SEQ ID NO: 4) and said virus is Marburg virus.

6. A method of treating a coagulopathy in a mammal with a viral hemorrhagic fever which comprises administering to said mammal an effective amount of a Nematode-Extracted Anticoagulant Protein ("NAP") having Factor VIIa/tissue factor inhibitory activity ("fVIIa/TF"), wherein said NAP comprises one or more NAP domains, wherein each NAP domain includes the sequence: Cys-A1-Cys-A2-Cys-A3-Cys-A4-Cys-A5-Cys-A6-Cys-A7-Cys-A8-Cys-A9-Cys-A10, wherein (a) A1 is an amino acid sequence of 7 to 8 amino acid residues;
(b) A2 is an amino acid sequence of 3 to 5 amino acid residues;
(c) A3 is an amino acid sequence of 3 amino acid residues;
(d) A4 is an amino acid sequence of 6 to 19 amino acid residues;
(e) A5 is an amino acid sequence of 3 to 4 amino acid residues;
(f) A6 is an amino acid sequence of 3 to 5 amino acid residues;
(g) A7 is an amino acid;
(h) A8 is an amino acid sequence of 11 to 12 amino acid residues;
(i) A9 is an amino acid sequence of 5 to 7 amino acid residues; and
(j) A10 is an amino acid sequence of 5 to 25 amino acid residues.

7. A method according to claim 6 wherein said virus is selected from the group consisting of Filoviridae, Arenaviridae, Bunyaviridae and Flaviridae.

8. A method according to claim 7 wherein said virus is from the family Filoviridae.

9. A method according to claim 8 wherein said NAP is AcaNAPc2 (SEQ ID NO:3) and said virus is Marburg virus.

10. A method according to claim 8 wherein said NAP is AcaNAPc2/proline (SEQ ID NO:4) and said virus is Marburg virus.

11. A method of treating an inflammatory response in a mammal with a viral hemorrhagic fever which comprises administering to said mammal an effective amount of a Nematode-Extracted Anticoagulant Protein ("NAP") having Factor VIIa/tissue factor inhibitory activity ("fVIIa/TF"), wherein said NAP comprises one or more NAP domains, wherein each NAP domain includes the sequence: Cys-A1-Cys-A2-Cys-A3-Cys-A4-cys-A5-Cys-A6-Cys-A7-Cys-A8-Cys-A9-cys-A10, wherein (a) A1 is an amino acid sequence of 7 to 8 amino acid residues;
(b) A2 is an amino acid sequence of 3 to 5 amino acid residues;
(c) A3 is an amino acid sequence of 3 amino acid residues;
(d) A4 is an amino acid sequence of 6 to 19 amino acid residues;
(e) A5 is an amino acid sequence of 3 to 4 amino acid residues;
(f) A6 is an amino acid sequence of 3 to 5 amino acid residues;
(g) A7 is an amino acid;

(h) A8 is an amino acid sequence of 11 to 12 amino acid residues;
(i) A9 is an amino acid sequence of 5 to 7 amino acid residues; and
(j) A10 is an amino acid sequence of 5 to 25 amino acid residues.

12. A method according to claim 11, wherein said virus is selected from the group consisting of Filoviridae, Arenaviridae, Bunyaviridae and Flaviridae.

13. A method according to claim 12 wherein said virus is from the family Filoviridae.

14. A method according to claim 13 wherein said NAP is AcaNAPc2 (SEQ ID NO:3) and said virus is Marburg virus.

15. A method according to claim 13 wherein said NAP is AcaNAPc2/proline (SEQ ID NO:4) and said virus is Marburg virus.

* * * * *